United States Patent
Li et al.

(10) Patent No.: US 11,654,288 B2
(45) Date of Patent: May 23, 2023

(54) SYSTEMS AND METHODS FOR MANAGING ATRIAL-VENTRICULAR DELAY ADJUSTMENTS

(71) Applicant: Pacesetter, Inc., Sylmar, CA (US)

(72) Inventors: Wenwen Li, San Jose, CA (US); Nima Badie, Berkeley, CA (US); Luke C. McSpadden, Los Angeles, CA (US); Yun Qiao, Sunnyvale, CA (US); Avi Fischer, New Rochelle, NY (US); Kyungmoo Ryu, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 16/988,821

(22) Filed: Aug. 10, 2020

(65) Prior Publication Data
US 2022/0040484 A1 Feb. 10, 2022

(51) Int. Cl.
*A61N 1/368* (2006.01)
*A61N 1/05* (2006.01)

(52) U.S. Cl.
CPC ......... *A61N 1/3682* (2013.01); *A61N 1/0587* (2013.01); *A61N 1/36843* (2017.08)

(58) Field of Classification Search
CPC . A61N 1/0587; A61N 1/3682; A61N 1/36843
See application file for complete search history.

(56) References Cited

U.S. PATENT DOCUMENTS

2019/0111270 A1* 4/2019 Zhou ................ A61B 5/349
2020/0179705 A1* 6/2020 Ternes ............... A61N 1/3702

OTHER PUBLICATIONS

Vijayaraman et al. "Prospective Evaluation of Feasibility and Electrophysiologic and Echocardiographic Characteristics of Left Bundle Branch Area Pacing" Heart Rhythm, 2019. 16(12): 9 pages.
Wang et al. "Feasibility and Efficacy of His Bundle Pacing or Left Bundle Pacing Combined With Atrioventricular Node Ablation in Patients With Persistent Atrial Fibrillation and Implantable Cardioverter-Defibrillator Therapy" J Am Heart Assoc, 2019. 8(24): 12 pages.
Lustgarten et al. "His-bundle Pacing Versus Biventricular Pacing in Cardiac Resynchronization Therapy Patients: A Crossover Design Comparison." Heart rhythm 12.7 (2015): 10 pages.

(Continued)

*Primary Examiner* — Michael W Kahelin
(74) *Attorney, Agent, or Firm* — The Small Patent Law Group LLC; Dean D. Small

(57) ABSTRACT

A system and method are provided for managing atrial-ventricular (AV) delay adjustments. An AV interval is measured that corresponds to an interval between an atrial paced (Ap) event or an atrial sensed (As) event and a sensed ventricular (Vs) event. A candidate AV delay is set based on the AV interval and a bundle branch adjustment (BBA) value. A QRS characteristic of interest (COI) is measured while utilizing the candidate AV delay in connection with delivering a pacing therapy. The BBA value is adjusted and the candidate AV delay is reset based on the BBA value as adjusted. A collection of QRS COIs and corresponding candidate AV delays are obtained and one of the candidate AV delays is selected as a BBA AV delay. The pacing therapy is managed, based on the BBA AV delay.

30 Claims, 9 Drawing Sheets

(56) References Cited

OTHER PUBLICATIONS

Teng et al. "Usefulness of His Bundle Pacing to Achieve Electrical Resynchronization in Patients with Complete Left Bundle Branch Block and the Relation Between Native QRS Axis, Duration, and Normalization" The American journal of cardiology 118.4 (2016): 17 pages.

Vijayaraman et al. "His-Optimized Cardiac Resynchronization Therapy to Maximize Electrical Resynchronization: A Feasibility Study." Circulation: Arrhythmia and Electrophysiology 12.2 (2019): 9 pages.

\* cited by examiner

SYSTEMS AND METHODS FOR MANAGING ATRIAL-VENTRICULAR DELAY ADJUSTMENTS

RELATED APPLICATIONS

The present application relates priority to U.S. Published application Ser. No. 16/574,959, titled "METHOD AND SYSTEM UTILIZING A PERCENTAGE-BASED ATRIO-VENTRICULAR DELAY ADJUSTMENT", filed Sep. 18, 2019, claiming priority to provisional application 62/734,830, filed Sep. 21, 2018; and U.S. Published application Ser. No. 16/574,930, titled "METHOD AND SYSTEM FOR DYNAMIC DEVICE-BASED ADJUSTMENT", filed Sep. 18, 2019, claiming priority to provisional application 62/734,817, filed Sep. 21, 2018; the complete subject matter of which are expressly incorporated herein by reference in their entireties.

FIELD

This disclosure relates generally to implantable cardiac stimulating devices.

BACKGROUND

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (AV) node and a ventricular conduction system comprised of the bundle of HIS (also referred to as the HIS bundle), the left and right bundle branches, and the Purkinje fibers, causing a depolarization and the resulting ventricular chamber contractions. The depolarization of the interventricular septum and ventricles is generally referred to as a QRS complex and is observed and measured through the use of electrocardiograms (ECGs) and similar equipment for measuring electrical activity of the heart.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or other anti-arrhythmia therapies to the heart, via electrodes implanted in contact with the heart tissue, at a desired energy and rate. To the extent the electrical pulses are sufficient to induce depolarization of the associated heart tissue, the heart tissue is said to be captured and the minimum electrical pulse resulting in capture is generally referred to as the capture threshold.

In the majority of individuals, the most effective heartbeat is triggered by the patient's own natural pacing physiology. Implantable cardiac stimulation devices are intended to fill in when the natural pacing functionality of the patient's heart fails or acts inefficiently (such as in cases of sinus arrest and symptomatic bradycardia, respectively) or when the heart's conduction system fails or acts inefficiently. In a large number of heart failure patients, natural conduction through the AV node and the HIS bundle are intact and disruption of ventricular rhythm is the result of conduction disorders residing in the left and/or right bundle branches.

Dilatation of the heart due to congestive heart failure (CHF) has been associated with delayed conduction through the ventricles. This delayed conduction leads to reduced hemodynamic efficiency of the failing heart because of the resulting poor synchronization of the heart chambers.

Direct stimulation of the HIS bundle has been found to provide hemodynamic improvement for various patients including those suffering from dilated cardiomyopathy but having normal ventricular activation. However, a significant learning curve remains in connection with the implant procedure and in some instances involves a higher rate of lead placement adjustment. HBP is also associated with higher capture thresholds and lower ventricular sensing amplitudes as compared so other pacing modes, which can be challenging for device functionality and battery longevity.

Further, HBP may exhibit lower success in patients with His-Purkinje conduction disease when the conduction block is more distal in the conduction system. Transvenous left bundle branch pacing (LBBP) has been proposed where the lead is implanted from the right ventricle and screwed deep into the septum to deliver pacing stimuli at the left bundle branch (LBB). The LBBP technique has been shown to be associated with an easier implant procedure, lower capture thresholds, and higher ventricular sensing amplitudes compared to HBP. LBBP has been proposed to be used in parallel or in lieu of HBP to increase overall success of physiological pacing.

The typical 12-lead ECG response during LBBP resembles a right bundle branch block (RBBB) pattern. It is desirable to optimize AV delay (atrial to LBBP delay) for the LBBP approach for a few reasons: 1) synchronizing LBBP with patient's intrinsic right bundle branch conduction mimics physiologic His-Purkinje system conduction; and 2) allowing the atrial kick to complete before ventricular activation maximizes LV ejection fraction for HF patients.

Moderate success has been demonstrated for HBP in correcting electrical dyssynchrony by recruiting diseased portions of conduction system and narrowing the QRS in patients with bundle branch block (BBB). However, the location of the conduction block plays a determining role in the ability to achieve BBB correction with HBP.

In addition, devices have been implemented that provide cardiac resynchronization therapy (CRT). In at least some CRT devices, one lead is located in the right atrium (RA), a second lead is located in the right ventricle (RV) and a third lead is located in a vein along the left ventricle (LV). The timing between the RA, RV and LV leads is managed to achieve a desired atrial ventricular (AV) delay. In one approach, the AV delay is further modified with an offset, in some instances referred to as a AV offset, to further manage timing between a paced/intrinsic event in the RA and a paced event in the RV.

BRIEF SUMMARY OF THE DISCLOSURE

In accordance with embodiments herein, a system for managing atrial-ventricular (AV) delay adjustments is provided. The system includes electrodes configured to be located proximate to an atrial (A) site and at least one of a left bundle branch (LBB) site or a HIS site. An implantable medical device (IMD) has a header that includes a right atrial (RA) header port, a right ventricular (RV) header port and a left ventricular (LV) header port. The system includes memory configured to store program instructions and one or more processors that, when configured to execute the program instructions measure an AV interval corresponding to an interval between an atrial paced (Ap) event or an atrial sensed (As) event and a sensed ventricular (Vs) event. The system sets a candidate AV delay based on the AV interval and a bundle branch adjustment (BBA) value, measures a QRS characteristic of interest (COI) while utilizing the candidate AV delay in connection with delivering a pacing therapy by the IMD and adjusts the BBA value and reset the candidate AV delay based on the BBA value as adjusted. The system repeats the adjust, reset and measure to obtain a collection of QRS COIs and corresponding candidate AV delays, selects one of the candidate AV delays, that corresponds to a select one of the QRS COIs, as a BBA AV delay and manages the pacing therapy, utilized by the IMD, based on the BBA AV delay.

Optionally, the one or more processors may be configured, when executing the program instructions, to implement, as the pacing therapy, a DDD mode pacing therapy. The system may further comprise a first lead including, as one of the electrodes, an LBB electrode configured to be implanted through a septal wall to a depth sufficient to be located proximate to the LBB site. The first lead may include a proximal terminal configured to connect the LBB electrode to the RV header port. The system may include a sensing circuitry configured to sense cardiac activity (CA) signals over an RV sensing channel, associated with the RV header port. The CA signals may be collected along a sensing vector defined at least in part by the LBB electrode. The measure, adjust, repeat, and select operations may be based in part on the CA signals.

Optionally, the one or more processors may be further configured to select the one of the candidate AV delays that manages delivery of pacing pulses at the LBB site at a select point in time before an intrinsic wave front is expected to propagate to or beyond a corresponding point along a right bundle branch. The one or more processors may be further configured to select the one of the candidate AV delays that resulted in a narrowest QRS duration within the collection of QRS COIs. The one or more processors may be further configured to adjust the candidate AV delay by subtracting, from the AV interval, multiple candidate BBA values in order to time delivery of pacing pulses at the LBB site at a point in time fused with intrinsic waveform propagation to or beyond a corresponding point along a right bundle branch.

Optionally, the system may comprise a first lead including, as one of the electrodes, an LBB electrode configured to be implanted through a septal wall to a depth sufficient to be located proximate to the LBB site. The first lead may include a proximal terminal configured to connect the LBB electrode to the LV header port. The pacing therapy may correspond to a cardiac resynchronization therapy (CRT) pacing therapy configured to deliver pacing pulses through the LV header port of the IMD to the LBB electrode configured to be implanted through the septal wall to a depth sufficient to be located proximate to the LBB site.

Optionally, the one or more processors may be further configured to set, as the candidate AV delay, a candidate A-LV delay by adjusting the AV interval based on an AV offset and further subtracting a VV delay from the AV interval. The VV delay may correspond to the BBA value. The adjusting may further comprise utilizing multiple candidate BBA values in order to time delivery of pacing pulses at the LBB site at a point in time fused with intrinsic waveform propagation to or beyond a corresponding point along a right bundle branch. The one or more processors may further be configured to select the one of the candidate AV delays that manages delivery of pacing pulses at the LBB site at a select point in time after an intrinsic wave front is expected to propagate to or beyond a corresponding point along a right bundle branch.

Optionally, the system may comprise a lead including a HIS electrode configured to be located at the HIS site. The lead may include a proximal terminal configured to connect the HIS electrode to the LV header port. The system may include a sensing circuitry configured to sense cardiac activity (CA) signals over an LV sensing channel associated with the LV header port. The CA signals may be collected along a sensing vector defined at least in part by the HIS electrode. The candidate AV delay and BBA AV delays may correspond to candidate atrial-HIS (AH) delays and BBA AH delays, respectively, following a new As or Ap event before a pacing stimulus is delivered through the LV header port to the HIS site.

Optionally, the BBA value may correspond to a VV delay. The candidate AV delay may be based on a difference between the AV interval, and AV offset and the VV delay. The one or more processors may be further configured to adjust the BBA value based on multiple VV delays and resetting the candidate AV delay based on each of the corresponding multiple VV delays. The one or more processors may be further configured to select the candidate AV delay having a corresponding VV delay that achieves the select one of the QRS COIs. The BBA AV delay may correspond to a BBA A-LV (HIS) delay representing a delay following a new As or Ap event before a pacing stimulus is delivered through the LV header port to the HIS site.

Optionally, the system may include a lead including a HIS electrode configured to be located at the HIS site. The lead includes a proximal terminal configured to connect the HIS electrode to the RV header port. The system may include a sensing circuit configured to sense cardiac activity (CA) signals over an RV sensing channel associated with the RV header port. The CA signals may be collected along a sensing vector defined at least in part by the HIS electrode. The candidate AV delays, and BBA AV delays may follow a new As or Ap event before a pacing stimulus is delivered through the RV header port to the HIS site.

In accordance with embodiments herein, a method for managing atrial-ventricular (AV) delay adjustments is provided. The method includes providing electrodes configured to be located proximate to an atrial (A) site and at least one of a left bundle branch (LBB) site or a HIS site. The method utilizes one or more processors for measuring an AV interval corresponding to an interval between an atrial paced (Ap) event or an atrial sensed (As) event and a sensed ventricular (Vs) event. The method sets a candidate AV delay based on the AV interval and a bundle branch adjustment (BBA) value, measures a QRS characteristic of interest (COI) while utilizing the candidate AV delay in connection with delivering a pacing therapy by an implantable medical device (IMD) and adjusts the BBA value and resets the candidate AV delay based on the BBA value as adjusted. The method repeats repeating the adjusting, resetting and measuring to obtain a collection of QRS COIs and corresponding candidate AV delays, selects one of the candidate AV delays, that corresponds to a select one of the QRS COIs, as a BBA AV delay and manages the pacing therapy, utilized by the IMD, based on the BBA AV delay.

Optionally, the pacing therapy may correspond to a DDD mode pacing therapy. The method may further comprises providing an LBB electrode configured to be implanted through a septal wall to a depth sufficient to be located proximate to the LBB site, connecting the LBB electrode to an RV header port, sensing cardiac activity (CA) signals over an RV sensing channel where the CA signals are collected along a sensing vector defined at least in part by the LBB electrode. The selecting may comprise selecting the one of the candidate AV delays that manages delivery of pacing pulses at the LBB site at a select point in time before an intrinsic wave front is expected to propagate to or beyond a corresponding point along a right bundle branch. The adjusting the candidate AV delay may include subtracting, from the AV interval, multiple candidate BBA values in order to time delivery of pacing pulses at the LBB site at a point in time fused with intrinsic waveform propagation to or beyond a corresponding point along a right bundle branch.

Optionally, the pacing therapy may correspond to a cardiac resynchronization therapy (CRT) pacing therapy configured to deliver pacing pulses through an LV header port of the IMD to an LBB electrode configured to be implanted through the septal wall to a depth sufficient to be located proximate to the LBB site. The setting the candidate AV delay may further comprise setting a candidate A-LV delay by adjusting the AV interval based on an AV offset and further subtracting a VV delay from the AV interval. The VV delay may correspond to the BBA value. The adjusting may further comprise utilizing multiple candidate BBA values in order to time delivery of pacing pulses at the LBB site at a point in time fused with intrinsic waveform propagation to or beyond a corresponding point along the right bundle branch.

Optionally, the method may provide a HIS electrode configured to be located at the HIS site. The method may connect the HIS electrode to a LV header port, sense cardiac activity (CA) signals over an LV sensing channel where the CA signals are collected along a sensing vector defined at least in part by the HIS electrode. The candidate AV delays, and BBA AV delays may correspond to candidate atrial-HIS (AH) delays and BBA AH delays, respectively, following a new As or Ap event before a pacing stimulus is delivered through the LV header port to the HIS site. The BBA value may correspond to a VV delay. The candidate AV delay may be based on a difference between the AV interval, and AV offset and the VV delay. The adjusting may further comprise adjusting the BBA value based on multiple VV delays and resetting the candidate AV delay based on each of the corresponding multiple VV delays.

Optionally, the selecting may further comprise selecting the candidate AV delay having a corresponding VV delay that achieves the select one of the QRS COIs. The BBA AV delay may correspond to a BBA A-LV (HIS) delay representing a delay following a new As or Ap event before a pacing stimulus is delivered through the LV header port to the HIS site. The method may provide a HIS electrode configured to be located at the HIS site. The method may connect the HIS electrode to a RV header port, sense cardiac activity (CA) signals over an RV sensing channel where the CA signals are collected along a sensing vector defined at least in part by the HIS electrode. The candidate AV delays and BBA AV delays may follow a new As or Ap event before a pacing stimulus is delivered through the RV header port to the HIS site.

BRIEF DESCRIPTION OF THE DRAWINGS

The various features of the present disclosure and the manner of attaining them will be described in greater detail with reference to the following description, claims, and drawings, wherein reference numerals are reused, where appropriate, to indicate a correspondence between the referenced items, and wherein:

DETAILED DESCRIPTION

Figure 1A:
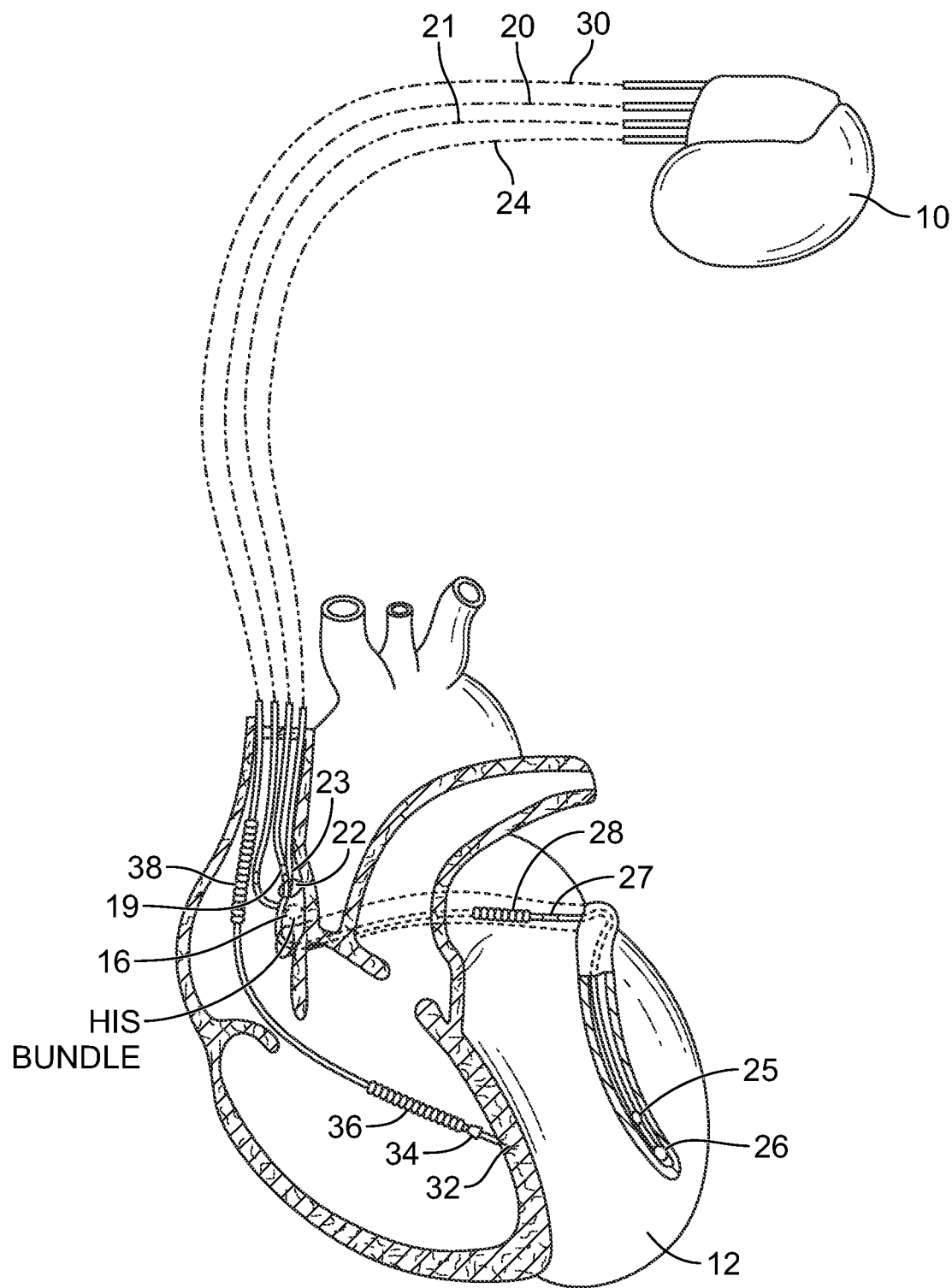
FIG. 1A is a simplified, partly cutaway view illustrating an implantable stimulation device in electrical communication with at least four leads, including a HIS Bundle lead, implanted into a patient's heart for delivering multi-chamber stimulation and shock therapy.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

The term "As-Vs interval", as used herein, refers to a measured intrinsic conduction time from a sensed atrial (As) event to a sensed ventricular (Vs) event. The sensed ventricular event may be a right ventricular event or a left ventricular event. The term "Ap-Vs interval", as used herein, refers to a measured intrinsic conduction time from a paced atrial (Ap) event to a sensed ventricular (Vs) event. The sensed ventricular event may be a right ventricular event or a left ventricular event.

The term "As-RVs interval", as used herein, refers to a measured intrinsic conduction time from a sensed atrial (As) event to a sensed right ventricular (RVs) event. The term "Ap-RVs interval", as used herein, refers to a measured intrinsic conduction time from a paced atrial (Ap) event to a sensed right ventricular (RVs) event.

The term "As-LVs interval", as used herein, refers to a measured intrinsic conduction time from a sensed atrial (As) event to a sensed left ventricular (LVs) event. The term "Ap-LVs interval", as used herein, refers to a measured intrinsic conduction time from a paced atrial (Ap) event to a sensed left ventricular (LVs) event.

The terms "atrioventricular delay" and "AVD" refer to a programmed time delay to be used by the implantable medical device in connection with delivering therapy.

The terms "AVD" and "AV delay" refer to an AVD in connection with delivering therapy at a ventricular site following a sensed or paced atrial event, when an intrinsic ventricular event does not occur before AVDs expires.

The terms "A-LVD" and "A-LV delay" refer to an AVD in connection with delivering therapy at a left ventricular site following a sensed or paced atrial event, when an intrinsic left ventricular event does not occur before A-LVD expires.

The term "LV only pacing" refers to a mode of operation for an implanted medical device in which the LV is paced but the RV is not paced.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

The present disclosure is directed to various aspects of stimulation devices and corresponding methods related to LBB and HIS bundle pacing. Aspects of the present disclosure may be implemented in a dual chamber, cardiac resynchronization therapy and/or other implantable devices. Embodiments herein may be implemented in connection with the methods, systems and devices described in U.S. patent application Ser. No. 16/871,166, titled "SYSTEMS AND METHODS FOR IMPROVED his BUNDLE AND BACKUP PACING TIMING" and filed May 11, 2020, the complete subject matter of which is incorporated herein by reference.

Certain cardiac pacemakers and defibrillators incorporate a pacing lead in the right ventricle and may also include a second lead in the right atrium. High-burden right ventricle pacing may contribute to the development of pacing-induced cardiomyopathy and symptoms associated with heart failure (HF). Several pathophysiologic mechanisms have been implicated in the development of pacing-induced HF, each of which likely stems from non-physiological electrical and mechanical activation patterns produced by right ventricle pacing. HIS bundle pacing (HBP) may restore physiological activation patterns by utilizing a patient's intrinsic conduction system and may do so even in the presence of bundle branch block. HBP has also been shown to provide significant QRS narrowing, with improved ejection fraction.

Conventional CRT systems include pacing from both a right ventricular and a left ventricular lead and have been shown most effective for patients exhibiting a wide QRS complex and left bundle branch block. HBP has also been shown to be effective at narrowing the QRS complex in patients with left bundle branch block, likely due to restoration of conduction through HIS and Purkinje, which includes right and left bundle fibers that are longitudinally dissociated. Therefore, what is thought of as left bundle branch block, can be a result of a proximal blockage within the HIS bundle that eventually branches to the left bundle. As a result, by pacing the HIS bundle distal to the blockage, a normalized QRS complex can be achieved in some patients. Theoretically, this pacing mode may provide even better results than known CRT treatments, as activation propagates rapidly through natural conduction pathways.

Overview of HBP System and Components

FIG. 1A illustrates a stimulation device 10 in electrical communication with a patient's heart 12 by way of four leads, 20, 21, 24, and 30 and suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage or atrial septum.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode within the coronary veins overlying the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus which overlies the left ventricle.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. In another embodiment, an additional electrode for providing left ventricular defibrillation shocking therapy may be included in the portion of the lead overlying the left ventricle, adjacent to the ring electrode 25.

The stimulation device 10 is generally configured as an implantable cardioverter-defibrillator (ICD) and generally includes functionality for pacing, sensing, and providing defibrillation to a patient heart. It should be appreciated however, that the ICD is just one example stimulation device that may implement aspects of the present disclosure. Other configurations and types of implantable stimulation devices incorporating aspects of the present disclosure are also contemplated. For example and without limitation, in at least one implementation, the stimulation device 10 may instead be configured as a pacemaker without defibrillation functionality and, in particular, a pacemaker configured to provide cardiac resynchronization therapy (CRT). In such implementations, some or all of the defibrillation coils illustrated and their associated circuitry within the stimulation device 10 may be omitted. It should also be appreciated that the specific configuration of leads and placement of leads illustrated in FIG. 1A is intended merely as an example and other configurations are possible. For example, in one specific implementation, the coronary sinus lead 24 may instead be replaced with a left ventricle lead that extends and is implanted within the left ventricle for pacing and/or sensing of the left ventricle. More generally, implementations of the present disclosure are generally applicable to any suitable stimulation devices currently known or later developed that provide HIS bundle pacing.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular coil electrode 36, and a superior vena cava (SVC) coil electrode 38. Typically, the right ventricular lead 30 is transvenously inserted into the heart 12 so as to place the right ventricular tip electrode 32 in the right ventricular apex so that the right ventricular coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

The stimulation device 10 is further connected to a HIS bundle lead 21 having a HIS tip electrode 16, such as a helical active fixation device, and a HIS ring electrode 19 located proximal from the HIS tip electrode 16. In certain implementations, the HIS ring electrode 19 is located approximately 10 mm proximal the HIS tip electrode 16. The HIS bundle lead 21 may be transvenously inserted into the heart 12 so that the HIS tip electrode 16 is positioned in the tissue of the HIS bundle. Accordingly, the HIS bundle lead 21 is capable of receiving depolarization signals propagated in the HIS bundle and exiting the Purkinje fibers to the myocardium or delivering stimulation to the HIS bundle, creating a depolarization that can be propagated through the lower conductive pathways of the right and left ventricles (i.e., the right and left bundle branches and Purkinje fibers).

The HIS bundle lead 21 will be described in greater detail in conjunction with FIGS. 5 and 6.

Figure 1B:
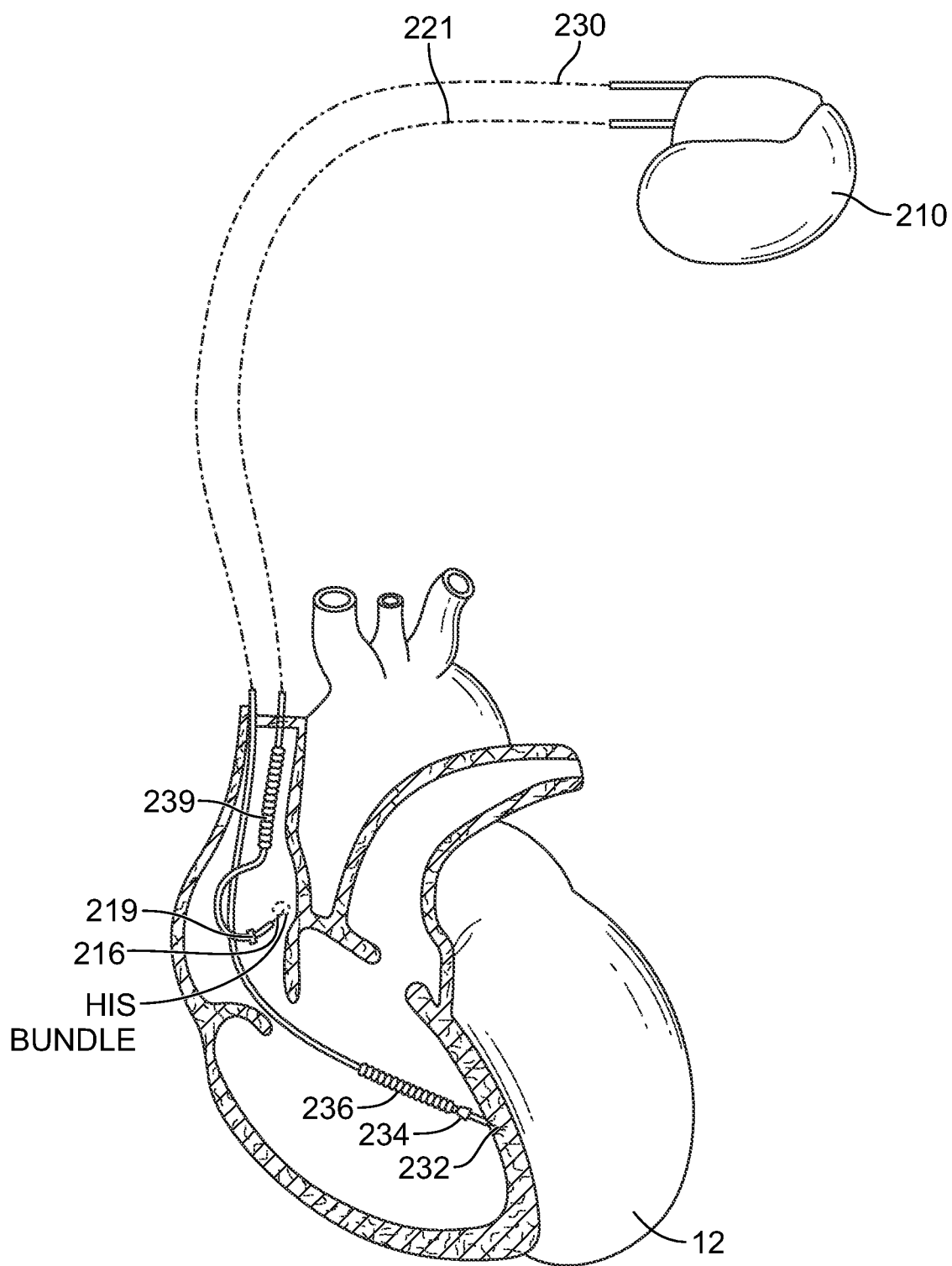
FIG. 1B is a simplified, partly cutaway view illustrating an alternative design of an implantable stimulation device, shown implanted into the right chambers of the patient's heart for delivering dual-chamber stimulation and shock therapy.

An alternative embodiment of the present disclosure is shown in FIG. 1B in which a dual chamber stimulation device 210 is in communication with one atrium, one ventricle, and the HIS bundle. A right atrial lead 20 can be optionally included. In such implementations, the stimulation device 210 maintains communication with the right atrium of the heart 12 via a right atrial lead 20 having at least an atrial tip electrode 22 and an atrial ring electrode 23, and an SVC coil electrode 239

A HIS bundle lead 221, having a HIS tip electrode 216 and a HIS ring electrode 219, is positioned such that the HIS tip electrode 216 is proximate the HIS bundle tissue. The stimulation device 210 is shown in FIG. 3 in electrical communication with the patient's heart 12 by way of a right ventricular lead 230 including a right ventricular tip electrode 232, a right ventricular ring electrode 234, and a right ventricular coil electrode 236.

Figure 2:
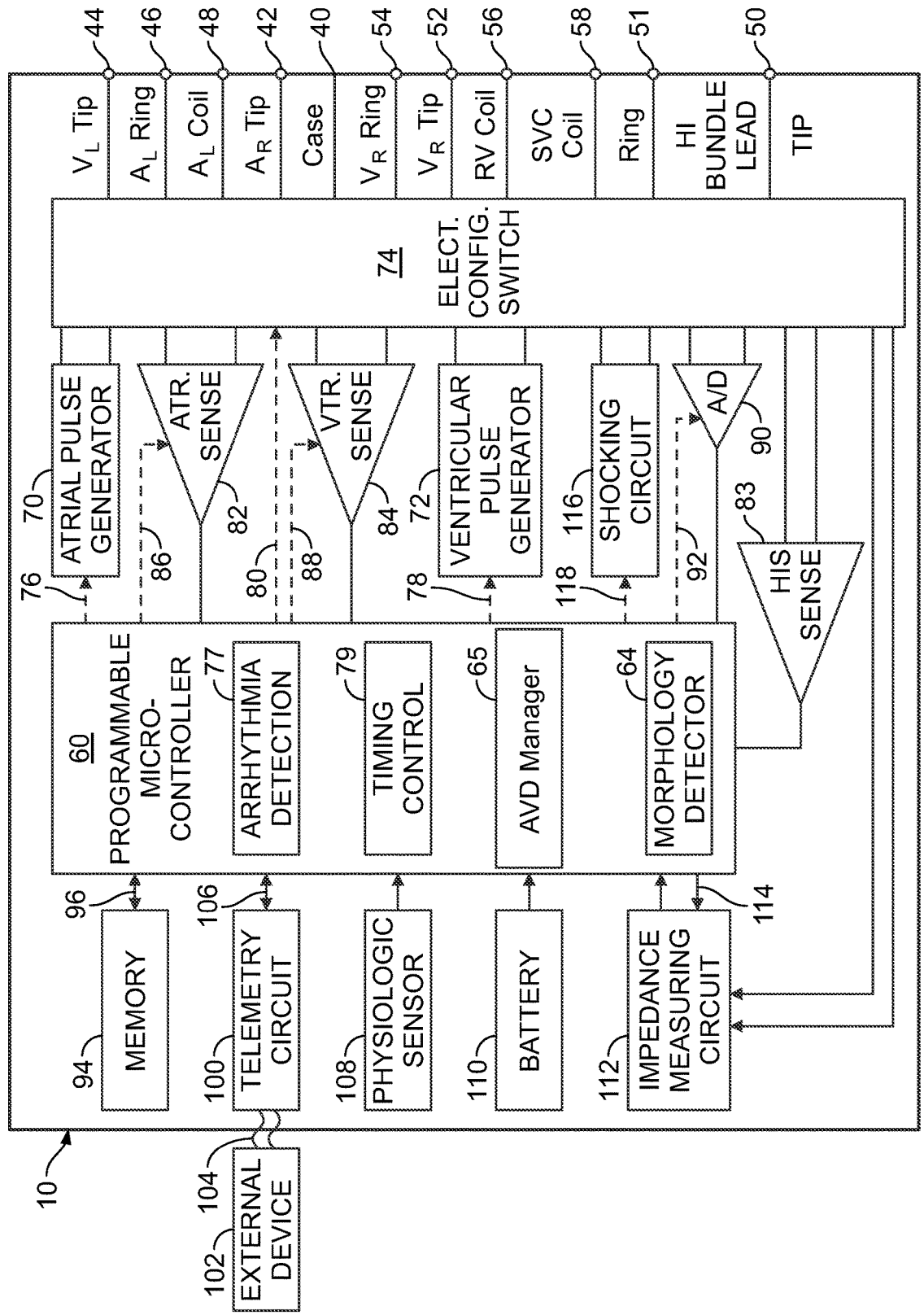
FIG. 2 illustrates a simplified block diagram of the multi-chamber implantable stimulation device, which is capable of treating both fast and slow arrhythmias with stimulation therapy, including cardioversion, defibrillation, and pacing stimulation.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10 is often referred to as the "can", "case" or "case electrode" and may be programmably selected to act as the return electrode for all "unipolar" modes. The housing 40 may further be used as a return electrode alone or in combination with one or more of the coil electrodes for shocking purposes. The housing 40 further includes a connector (not shown) having a plurality of terminals 42, 44, 46, 48, 50-52, 54, 56, and 58 (shown schematically and, for convenience, next to the names of the electrodes to which they are connected). To achieve right atrial sensing and pacing, the connector includes at least a right atrial tip terminal (AR TIP) 42 adapted for connection to the atrial tip electrode 22 (shown in FIG. 2).

To achieve left chamber sensing, pacing, and defibrillation (in applications in which the stimulation device 10 is an ICD), the connector includes at least a left ventricular tip terminal (VL TIP) 44, a left atrial ring terminal (AL RING) 46, and a left atrial shocking terminal (AL COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the right ventricular coil electrode 36, and the SVC coil electrode 38, respectively. To achieve HIS bundle sensing, or sensing and stimulation, the connector further includes a HIS bundle lead tip terminal 50 and a HIS bundle lead ring terminal 51 which are adapted for connection to the HIS tip electrode 16 and the HIS ring electrode 19, respectively.

At the core of the stimulation device 10 is a programmable microcontroller 60 which controls the various modes of stimulation therapy. The microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present disclosure. Rather, any suitable microcontroller 60 may be used that carries out the functions described herein.

An atrial pulse generator 70 and a ventricular pulse generator 72 generate pacing stimulation pulses for delivery via an electrode configuration switch 74. The atrial and ventricular pulse generators 70, 72 may include dedicated, independent pulse generators, multiplexed pulse generators, or shared pulse generators. The pulse generators 70, 72 are controlled by the microcontroller 60 via appropriate control signals 76, 78, respectively, to trigger or inhibit the stimulation pulses. The microcontroller 60 further includes timing control circuitry 79 which is used to control the timing of such stimulation pulses (e.g., pacing rate) as well as to keep track of the timing of refractory periods, blanking intervals, noise detection windows, evoked response windows, alert intervals, marker channel timing, etc., which is well known in the art.

The timing control circuitry 79 also controls the onset and duration of a HIS signal sensing window during which a depolarization signal conducted through the AV node to the HIS bundle can be detected. Timing control circuitry 79 also controls a timing delay provided after a detected HIS signal detection, prior to the delivery of a right and/or left ventricular stimulation pulse.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches (not shown) as is known in the art.

Atrial sensing circuits 82 and ventricular sensing circuits 84 may also be selectively coupled to various electrodes through the switch 74 for detecting the presence of cardiac activity along select sensing vectors. The electrodes may be distributed between the various leads positioned to different locations in or along the heart. As explained herein, in accordance with new and unique aspects herein, electrodes are configured to be located proximate to an atrial (A) site and at least one of a left bundle branch (LBB) site and/or a HIS site. The sensing circuits 82 and 84 are configured to sense cardiac activity (CA) signals over corresponding sensing channels associated with a corresponding port in the header of the IMD. For example, the header includes an RA header port, an RV header port and an LV header port. The sensing circuits 82 and 84 are connected to a desired one or more of the RA, RV and LV header ports. For example, the sensing circuit 82 may be connected to the RA header port, while one sensing circuit 84 is connected to the RV header port and another sensing circuit 84 is connected to the LV header port. Additionally or alternatively, a single sensing circuit 84 may be utilized in connection with both the RV and LV header ports, but switched between the RV and LV header ports through switch 74.

The outputs of the sensing circuits 82-84 are connected to the microcontroller 60 which, in turn, is able to trigger or inhibit the atrial and ventricular pulse generators 70, 72, respectively, in a demand fashion in response to the absence or presence of cardiac activity in the appropriate chambers of the heart. The atrial and ventricular sensing circuits 82, 84, in turn, receive control signals over signal lines 86, 88, from the microcontroller 60 for purposes of controlling the gain, threshold, polarization charge removal circuitry (not shown), and the timing of any blocking circuitry (not shown) coupled to the inputs of the sensing circuits 82, 84.

As explained herein, the sensing circuit 84 may be connected to an RV header port which is in turn connected to a lead having an electrode located proximate to an LBB site (e.g., an LBB sensing site and/or LBB pacing site). The sensing circuit 84 senses CA signals over a corresponding RV sensing channel, but the CA signals are collected along a sensing vector defined at least in part by the LBB electrode.

According to one implementation of the present disclosure, a HIS sensing circuit 83 is selectively coupled to the HIS bundle lead 21 for detecting the presence of a conducted depolarization arising in the atria and conducted through the HIS bundle via the AV node. As used herein, each of the atrial sensing circuit 82, the ventricular sensing circuit 84, and the HIS sensing circuit 83, includes a discriminator, which is a circuit that senses and can indicate or discriminate the origin of a cardiac signal in each of the cardiac chambers. The HIS sensing circuit 83 may be a dedicated circuit within the stimulation device 10 or His-related functionality may instead be provided by repurposing other pacing and sensing channels and circuitry of the stimulation device 10. For example, the stimulation device 10 may be reprogrammed such that a pacing channel, a sensing channel, and associated circuitry initially programmed for use in sensing and pacing one of the atria or ventricles may instead be reconfigured to pace and sense the HIS bundle.

Additionally or alternatively, the sensing circuit 84 may be utilized in connection with a lead including a HIS electrode configured to be located at the HIS site. The lead includes a proximal terminal configured to connect the HIS electrode to the LV header port. The sensing circuit 84 may be connected to the LV header port and configured to sense CA signals over an LV sensing channel associated with the LV header port, even though the CA signals are collected along a sensing vector defined at least in part by the HIS electrode.

Additionally or alternatively, the sensing circuit 84 may be utilized in connection with a lead including a HIS electrode configured to be located at the HIS site with the lead including a proximal terminal configured to connect the HIS electrode to the RV header port. The sensing circuit 84 may be connected to the RV header port and configured to sense cardiac activity (CA) signals over an RV sensing channel associated with the RV header port, wherein the CA signals are collected along a sensing vector defined at least in part by the HIS electrode.

Figure 3A:
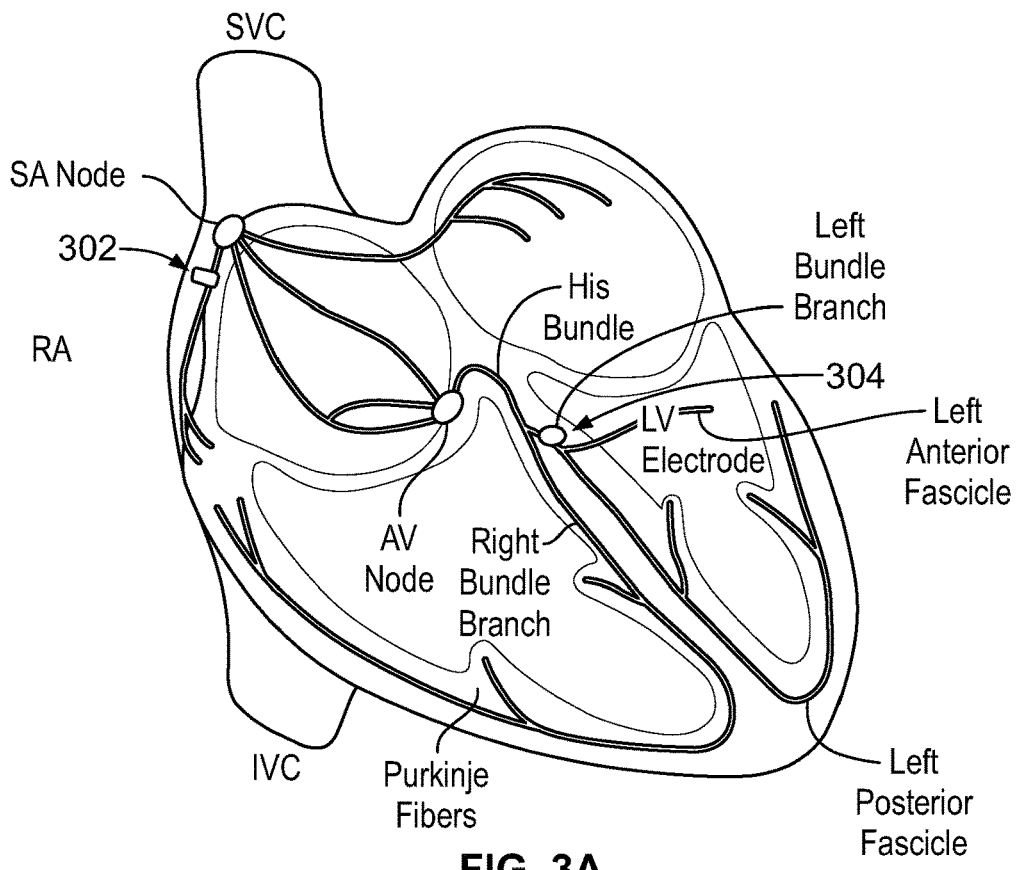
FIG. 3A illustrates a graphical representation of a heart with one or more electrodes located select pacing and sensing sites relative to the specialized conduction system in accordance with embodiments herein.

FIGS. 3A-3-D illustrate examples of different combinations of locations at which sensing and/or pacing electrodes may be positioned and utilized to collect CA signals in connection with sensing channels defined by the sensing circuits 82 and 84 and a corresponding connection to an RA, RV or LV header port.

The programmable controller 60 includes an AV delay manager 65 that is configured to implement the operations described herein, including operations described in connection with FIGS. 4A-4D. For example, the programmable controller 60 may represent one or more processors that are configured to execute program instructions to implement the AV delay manager 65 to perform one or more of the following operations: measure an AV interval corresponding to an interval between an atrial paced (Ap) event or an atrial sensed (As) event and a sensed ventricular (Vs) event; set a candidate AV delay based on the AV interval and a bundle branch adjustment (BBA) value; measure a QRS characteristic of interest (COI) while utilizing the candidate AV delay in connection with delivering a pacing therapy by an implantable medical device (IMD); adjust the BBA value and reset the candidate AV delay based on the BBA value as adjusted; repeat the adjust, reset and measure to obtain a collection of QRS COIs and corresponding candidate AV delays; select one of the candidate AV delays, that corresponds to a select one of the QRS COIs, as a BBA AV delay. The programmable controller 60 and the various circuits and modules associated there with are configured to manage the pacing therapy based on the BBA AV delay.

Additionally or alternatively, the AV delay manager 65 is configured to implement, as the pacing therapy, a DDD mode pacing therapy. The AV delay manager 65 is configured to process the CA signals, such as collected along a sensing vector defined at least in part by a LBB electrode and or a HIS electrode. Additionally or alternatively, the AV delay manager is configured to select the one of the candidate AV delays that manages delivery of pacing pulses at the LBB site at a select point in time before an intrinsic wave front is expected to propagate to or beyond a corresponding point along the right bundle branch. Additionally or alternatively, the AV delay manager 65 is configured to select the one of the candidate AV delays that resulted in a narrowest QRS duration within the collection of QRS COIs. Additionally or alternatively, the AV delay manager 65 is configured to adjust the candidate AV delay by subtracting, from the AV interval, multiple candidate BBA values in order to time delivery of pacing pulses at the LBB site at a point in time fused with intrinsic waveform propagates to or beyond a corresponding point along the right bundle branch. Additionally or alternatively, the AV delay manager is configured to set, as the candidate AV delay, a candidate A-LV delay by adjusting the AV interval based on an AV offset and further subtracting a VV delay from the AV interval, the VV delay corresponding to the BBA value, the adjusting further comprising utilizing multiple candidate BBA values in order to time delivery of pacing pulses at the LBB site at a point in time fused with intrinsic waveform propagates to or beyond a corresponding point along the right bundle branch. Additionally or alternatively, the AV delay manager 65 is configured to select the one of the candidate AV delays that manages delivery of pacing pulses at the LBB site at a select point in time after an intrinsic wave front is expected to propagate to or beyond a corresponding point along the right bundle branch.

Additionally or alternatively, the AV delay manager 65 is configured to utilize a BBA value that corresponds to a VV delay, the candidate AV delay based on a difference between the AV interval, and AV offset and the VV delay. The AV delay manager 65 further configured to adjust the BBA value based on multiple VV delays and resetting the candidate AV delay based on each of the corresponding multiple VV delays. Additionally or alternatively, the AV delay manager 65 is further configured to select the candidate AV delay having a corresponding VV delay that achieves the select one of the QRS COIs, the BBA AV delay corresponding to a BBA A-LV (HIS) delay representing a delay following a new As or Ap event before a pacing stimulus is delivered through the LV header port to the HIS site.

For arrhythmia detection, the stimulation device 10 includes an arrhythmia detector 77 that utilizes the atrial and ventricular sensing circuits 82, 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (AID) data acquisition system 90 represented by an A/D converter. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the HIS bundle lead 21, the coronary sinus lead 24, and the right ventricular lead 30 through the switch 74 to sample cardiac signals across any pair of desired electrodes.

In one embodiment, the data acquisition system 90 is coupled to microcontroller 60, or to other detection circuitry, for detecting a desired feature of the HIS bundle signal.

Advantageously, the data acquisition system 90 may be coupled to the microcontroller 60, or other detection circuitry, for detecting an evoked response from the heart 12 in response to an applied stimulus, thereby aiding in the detection of capture. The microcontroller 60 detects a depolarization signal during a window following a stimulation pulse, the presence of which indicates that capture has occurred. The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, trans-telephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In certain implementations, the stimulation device 10 may further include a physiologic sensor 108, commonly referred to as a "rate-responsive" sensor to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, stimulation delays, etc.) at which the atrial and ventricular pulse generators 70, 72 generate stimulation pulses.

The stimulation device 10 additionally includes a battery 110 which provides operating power to all of the circuits shown in FIG. 4. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The device 10 has an impedance measuring circuit 112 which is enabled by the microcontroller 60 via a control signal 114. The known uses for an impedance measuring circuit 112 include, but are not limited to, lead impedance surveillance during the acute and chronic phases for detecting proper lead positioning or dislodgement; detecting operable electrodes and conductors; and automatically switching to an operable pair if dislodgement or electrical disruption occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

According to one implementation of the present disclosure, the HIS tip electrode 16 and HIS ring electrode 19 may be selectively coupled via switch 74 to the impedance measuring circuit 112 for performing a tissue impedance measurement.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (for example, up to 0.5 joules), moderate (for example, 0.5-10 joules), or high energy (for example, 11-40 joules), as controlled by the microcontroller 60. Such shocking pulses are applied to the patient's heart 12 through at least two shocking electrodes, and as shown in this embodiment, selected from the left atrial coil electrode 28, the right ventricular coil electrode 36, and the SVC coil electrode 38. As noted above, the housing 40 may act as an active electrode in combination with the right ventricular electrode 36, or as part of a split electrical vector using the SVC coil electrode 38 or the left atrial coil electrode 28 (i.e., using the right ventricular electrode 36 as a common electrode). As previously noted, the implementation illustrated in FIG. 2 is provided as an example and other configurations are possible. For example, in other implementations, the high voltage coils for both RV coil and SVC coil may be disposed on the right ventricle lead as opposed to the RA lead.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

FIGS. 3A-3D illustrate models of the specialized conduction system as activated in accordance with embodiments herein to maintain physiologic pacing. The SA node is connected through the internodal tracts to the AV node. The AV node is in turn connected to the specialized conduction system that includes the bundle of HIS which branches into the right bundle branch (RBB) and left bundle branch (LBB). The RBB is connected to the Purkinje fibers, and the LBB branches into the posterior and anterior fascicles As explained herein, in accordance with new and unique aspects herein, electrodes are located at new and unique pacing/sensing locations relative to the specialized conduction system in various embodiments. The IMD includes a header having ports that are generally configured to receive the proximal ends of leads that are positioned in or along certain chambers of the heart, such as the RA, RV and LV. Similarly, the IMD is generally configured to process the CA signals coming from the corresponding RA, RV and LV ports as if such CA signals are associated with certain conventional sensing vectors through the corresponding one of the RA, RV and LV, respectively. Further, the IMD is generally configured to deliver pacing pulses through the RA, RV and LV ports with the expectation that such pacing pulses are delivered to electrodes located at one or more generally well-established pacing sites in the RA, RV and LV, respectively.

The IMD header does not have a separate port that is configured to be connected to electrodes located at the positions described herein in connection with the specialized conduction system, such as locations along the LBB, RBB and HIS. Consequently, a conventional IMD is not readily suited to utilize CA signals sensed from an LBB or HIS electrode for adjusting device timings. The conventional IMD is not readily suited to manage the timing in connection with delivery of pacing pulses at LBB or HIS pacing sites.

In accordance with new and unique aspects herein, the AV delay is adjusted based on certain offsets and, in some embodiments the AV delay is adjusted based on a VV delay, to account for the new pacing locations and in order to pace the LBB in a manner to activate the LBB at a point in time contemporaneous with an intrinsic wave front moving down the RBB. In accordance with new and unique aspects herein, embodiments are described to stimulate the LBB at a select time relative to an intrinsic waveform propagating along the RBB to activate the ventricles in a preferred physiologic manner. For example, in accordance with certain electrode configurations, the LBB is stimulated at a select point in time (also referred to as "fused") slightly before (e.g., such as 5 ms-20 ms, or more preferably between 5 ms and 10 ms) the intrinsic waveform passes through a corresponding segment of the RBB. Embodiments utilize various timing algorithms to determine when conduction occurs through the native specialized conduction system (e.g., HIS, RBB and LBB) and to deliver a pacing impulse appropriate timed to achieve fusion between the paced LBB stimulus and an intrinsic wave front propagating along the RBB.

In accordance with new and unique aspects herein, new approaches have been developed to sense and pace the specialized conduction system. The specialized conduction system represents a highly complex conduction system. Among other things, the LBB includes anterior and posterior fascicles that differ from the interconnection between the RBB and the Purkinje fibers. Embodiments herein utilize the anatomical determination of the sensing within the specialized conduction system to account for the fact that different patients will experience different levels of disease within the specialized conduction system which will affect conduction patterns and conduction rates through the specialized conduction system. Embodiments leverage the ability to sense at particular anatomic locations and to apply new parameters for adjusting timing delays to overcome abnormal baseline conduction experienced by a patient.

Dual Chamber Pacing with LBB Electrode

Next, a configuration is described in connection with an IMD configured to provide dual chamber pacing utilizing electrode configuration electrode located proximate to the LBB, but connected to the RV port in the header of the IMD.

FIG. 3A illustrates a graphical representation of a heart with one or more electrodes located select pacing and sensing sites relative to the specialized conduction system. Electrodes are located in the RA and in the septal wall proximate to the LBB in accordance with embodiments herein. For example, an RA electrode 302 is located proximate the SA node and an LBB electrode 304 is tunneled in the septal wall at a point and depth proximate to a proximal end of the LBB. The RV electrode 304 is located distal to the HIS bundle such that the LBB electrode 304 is positioned to induce an evoked response into a proximal portion of the LBB without substantially invoking an evoked response into the RBB. When the LBB electrode 304 is located proximate the LBB, the LBB electrode 304 is able to pace the LBB but sense an intrinsic LV basal/proximal activation instead of sensing a potential at the LBB.

The LBB electrode 304 is implanted through the septal wall to a depth sufficient to be located proximate to a proximal end of the LBB, and is not located at a traditional RV sensing site, such as proximate to the apex of the RV. The LBB electrode 304 is connected through the body of the corresponding lead to a contact located on a terminal at the proximal end of the lead. The terminal is plugged into an RV port at a header of the IMD. The IMD (and a baseline AV delay management algorithm) is generally configured to assume that CA signals, carried through a sensing channel associated with the RV header port, represent CA signals sensed by one or more RV electrodes. The IMD (and baseline AV delay management algorithm) is further generally configured to assume that, when the AV delay terminates, the stimulation output/applied to the RV header port will be delivered through a lead to one or more electrodes at an RV location intended to stimulate the RV.

In accordance with new and unique aspects herein, embodiments are configured to manage sensing and pacing utilizing electrode 304 located at an LBB sensing/pacing site that is at the proximal end of the LBB while coupled to the RV header port of the IMD.

Figure 4A:
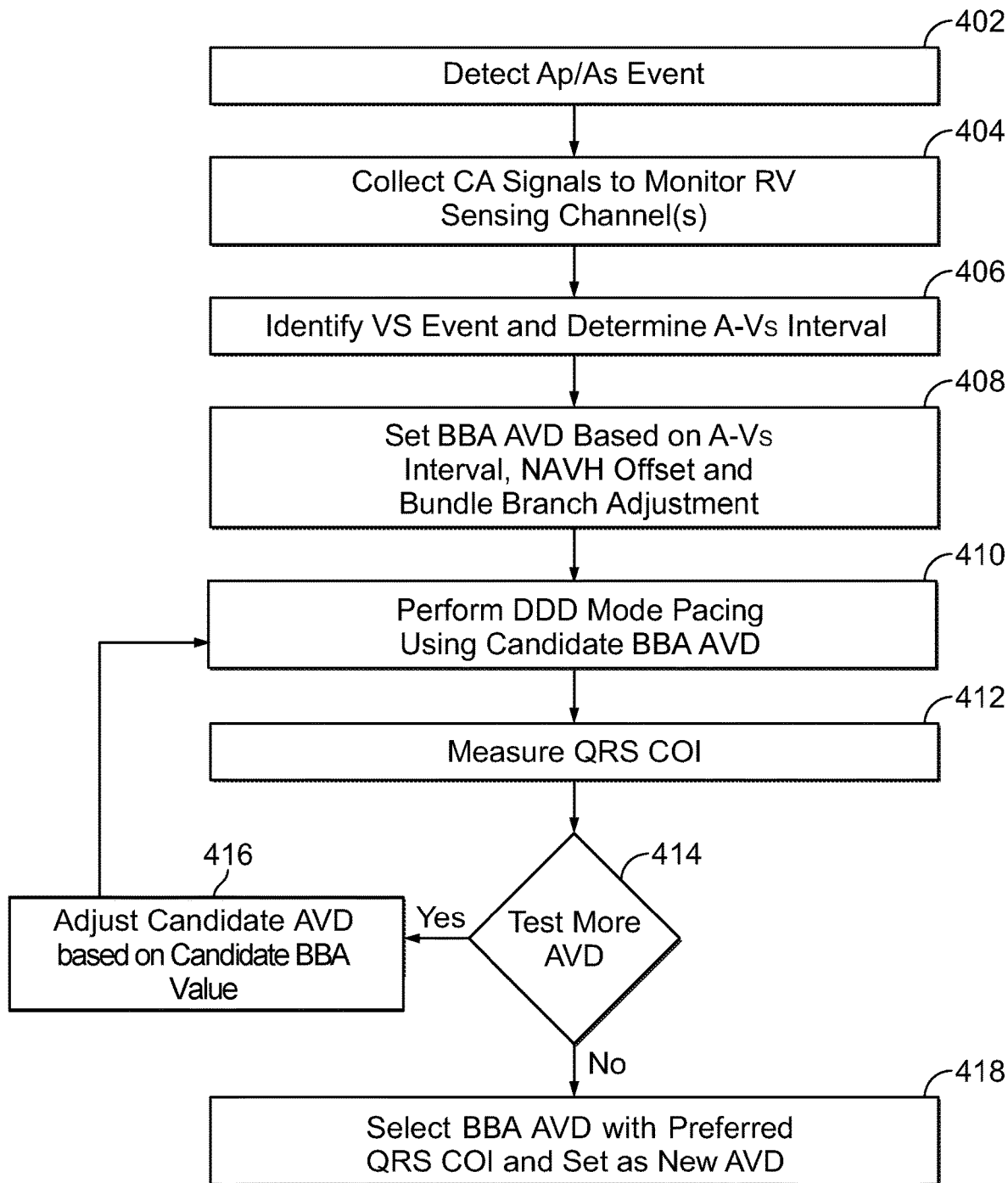
FIG. 4A illustrates a process for managing stimulation timing for the electrode configuration shown in FIG. 3A in accordance with embodiments herein.

FIG. 4A illustrates a process for managing stimulation timing for the electrode configuration shown in FIG. 3A in accordance with embodiments herein. In accordance with new and unique aspects herein, embodiments support connection of an LBB electrode to an RV header port while managing the AV delay management algorithm within the IMD to output/applied stimulation to the RV header port at a point in time when it is desirable for the stimulation to be delivered at a proximal end of the left bundle branch at a select point in time (e.g., fused) slightly before (e.g., such as 5 ms-20 ms, or more preferably between 5 ms and 10 ms) an intrinsic wave front propagates to or beyond a corresponding point along the right bundle branch. The process of FIG. 4A is implemented in connection with an IMD having leads implanted with electrodes at the positions noted in FIG. 3A, with the LBB electrode coupled to an RV header port. The IMD utilizes stimulation parameters associated with a "DDD" mode for the IMD. The stimulation parameters include an atrial-ventricular (AV) delay (AVD) that is defined based on a programmed or previously measured interval between an intrinsic or paced atrial event and an intrinsic ventricular event.

At 402, the one or more processors detect a paced atrial (Ap) event or sensed atrial (As) event over an atrial sensing channel utilizing an RA electrode (e.g., 302 in FIG. 3A). When the paced or sensed atrial event is detected, one or more interval timers are started.

At 404, the one or more processors monitor an RV sensing channel for cardiac activity signals. The RV sensing channel utilizes a sensing vector that is defined in part by an electrode located at a proximal end of the left bundle branch (e.g., the electrode 304 in FIG. 3A). Given that the sensing vector utilizes an electrode located along the LBB, a majority of the physical anatomy of the RV is somewhat tangential to the sensing vector. For example, in a bipolar sensing configuration, the sensing vector may extend between a combination of electrodes located on the lead that has the electrode located at the LBB. As another example, in a monopolar sensing configuration, the sensing vector may extend between a can or housing of the IMD and the electrode at the LBB. In both the monopolar and bipolar sensing configurations, a near field or primary portion of the sensing vector is located at the septal wall proximate to the proximal end of the LBB, while an apex of the RV is more distant from the sensing vector and may be considered to be in a midfield or secondary portion the sensing vector.

The CA signals collected over the sensing channel include a first signal component associated with the near field, such as evoked responses experienced at the proximal end of the left bundle branch. The CA signals will also include a second signal component associated with the midfield, such as ventricular (Vs) events. A VS event represents a depolarization signal experienced when the RV contracts and will represent a substantially larger signal than the first signal component corresponding to the evoked response at the proximal end of the LBB, even though a majority of the RV muscle is spaced a midfield distance from a center of the sensing vector. The terms "first" and "second" are used only to differentiate between respective items, and are not indicative of a priority, order in time, size, significance or otherwise. For example, in connection with certain pathologic conditions, the second signal component associated with the VS event may occur in time before the first signal component associated with the evoked response is experienced at the proximate end of the LBB. In some instances, a VS event may be sensed, while the LBB evoked response does not occur, and vice versa.

In the embodiment described in connection with FIG. 4A, the LBB evoked response is not necessarily measured or utilized to determine a direct timing interval between an atrial event and the LBB evoked response. Additionally or alternatively, the LBB evoked response may be directly measured from the CA signals and utilized to calculate an atrial-LBB interval between the paced or sensed atrial event and the evoked response occurring at the proximal end of the LBB. When it is desirable to detect the LBB evoked response, optionally, separate sensing channels may be utilized to collect CA signals associated with the first and second signal components. For example, CA signals sensed along a sensing vector that utilizes the electrode 304 may be supplied to two or more separate sensing circuits that are configured in different manners to be sensitive to corresponding signal components of interest. For example, the CA signals collected at the electrode 304 may be processed along a first sensing channel to identify the first signal component associated with the LBB evoked response, while the same or different CA signals collected at the electrode 304 may be processed along a second sensing channel to identify the second signal component associated with the VS event.

At 406, the one or more processors identify the second signal components, associated with the VS event, from the CA signals. The second signal component maybe identified by the one or more processors, while executing program instructions to analyze digitize CA signals. Additionally or alternatively, the second signal component maybe identified by the one or more processors based on a flag or other signal generated by firmware or hardware. For example, firmware or hardware may identify the VS event when an amplitude of the CA signals exceeds a second threshold within a VS event search window that is set at a predetermined period of time following the As/Ap event. Additionally or alternatively, when the LBB evoked response is of interest, firmware or hardware may identify the LBB evoked response when an amplitude of the CA signals exceeds a first threshold within an LBB search window that is set at a predetermined period of time following the As/Ap event.

Additionally, at 406, the one or more processors determine an atrial sensed/paced to ventricular sensed (A-VS) interval corresponding to the interval in time between the As or Ap event and the Vs event. Optionally, at 406, the one or more processors determine an atrial sensed/paced to LBB ER (A-LBB) interval corresponding to the interval in time between the As or Ap event and the LBB evoked response.

At 408, the one or more processors set the AV delay based on the A-VS interval. For example, the AV delay may be set to represent a percentage of the A-VS interval. As another example, the AV delay may be set to equal the A-VS interval with an offset subtracted there from, where the offset corresponds to a negative AV hysteresis (NAVH) to form a hysteresis corrected AVD. For example, the hysteresis corrected AVD may equals the A-VS interval minus the NAVH, where the NAVH represents a preprogrammed offset. Additionally or alternatively, the hysteresis corrected AVD may be set to equal the A-VS interval minus a percentage of the A-VS interval (e.g., 10%) where the percentage represents a NAVH percentage that is a preprogrammed offset.

At 408, the AVD is further adjusted based on a bundle branch adjustment to form a candidate BBA AV delay. The bundle branch adjustment may represent a preprogrammed value that is configured to delay or accelerate a time at which a stimulation pulse is delivered to the proximal end the LBB. For example, the bundle branch adjustment may be set to be longer, thereby further shortening the AVD, when it is desirable to pace at the LBB at an earlier point in time following the atrial event. Alternatively, the BBA may be set to be shorter, thereby only shortening the AVD by a small amount, when it is desirable to pace at the LBB at a later point in time following the atrial event. The BBA may be initially programmed by a clinician to a standardized value and/or based on a particular physiologic condition of the patient, such as the location of and amount of bundle branch block exhibited by the patient. The candidate BBA AV delay is configured to achieve fusion between conduction along the RBB and LBB such that the LBB is stimulated at a select point in time (fused) slightly (e.g., such as 5 ms— 20 ms, or more preferably between 5 ms and 10 ms) before an intrinsic waveform propagates to or beyond a corresponding point along the RBB.

At 410, the one or more processors modify the parameters of the DDD mode implemented by the IMD to utilize the candidate BBA AV delay.

At 412, the one or more processors manage the DDD mode of operation of the IMD utilizing the candidate BBA AV delay for one or more cardiac beats. At 412, the one or more processors further measure a QRS characteristic of interest (COI). For example, the QRS COI may correspond to a duration of the QRS. As another example, the QRS COI may correspond to a morphology of the QRS. The operations at 410 and 412 may be implanted in connection with a single cardiac beat or a desired number of beats. For example, the one or more processors may utilize the candidate BBA AV delay in connection with an ensemble of beats (e.g., 5-10). The QRS COI may be separately measured for each of the beats within the ensemble, and then combined through a select mathematical combination (e.g., averaging) to form an ensemble QRS COI. Alternatively, the ensemble of beats may be combined through a select mathematical combination (e.g., averaging), and then the one or more processors determines the QRS COI for the ensemble.

At 414, the one or more processors determine whether to perform more testing of candidate BBA AV delays. When further testing is desirable, flow moves to 416 where the adjusting operation is repeated for multiple candidate BBA values that are chosen in an attempt to identify a time delivery of pacing pulses at the LBB site at a point in time fused with intrinsic waveform propagates to or beyond a corresponding point along the right bundle branch. A candidate BBA AV delay is calculated in connection with each of the multiple BBA values.

At 416, the one or more processors adjust the candidate BBA AV delay, such as by incrementing or decrementing a stepped value of the candidate BBA AV delay by predetermined amounts. At 416, the one or more processors reset the candidate BBA AV delay based on the new value for the BBA VD delay delay. For example, during a first iteration through 416, the candidate BBA AV delay may be reduced by a select number of milliseconds (e.g., 5 ms). Thereafter, flow returns to 410 and the operations at 410 and 412 are repeated utilizing the adjusted candidate BBA AV delay. The operations at 410-416 are iteratively repeated to obtain a collection of QRS COI for a corresponding collection of candidate BBA AV delays. For example, the QRS duration may be measured for 10 different AV delays, from which 5 AV delays represent 5 ms steps below the candidate BBA AV delay determined at 408, and from which 5 AV delays represent 5 ms steps above the candidate BBA AVD determined at 408. Once a sufficient number of QRS COI are determined for incremental adjustments in the candidate BBA AV delays, flow moves to 418. At 418, the one or more processors review the QRS COI for the various corresponding adjustments in the candidate AVD to identify a preferred QRS COI. For example, the preferred QRS COI may correspond to the narrowest QRS duration within the collection. As another example, the preferred QRS COI may correspond to an intermediate QRS duration within the collection.

Additionally or alternatively, the QRS COI may correspond to a morphology of the QRS. As an example, a preferred QRS morphology may correspond to a maximum area under the curve for the QRS waveform, the QRS waveform exhibiting the largest peaks-valleys, the QRS waveform exhibiting a sharpest slope (e.g., maximum derivative) and the like.

At 418, a new BBA AV delay is set corresponding to an associated candidate BBA AV delay based on the preferred QRS COI. The new BBA AV delay may be automatically set by the one or more processors. Alternatively, the new BBA AV delay may be presented on a GUI of programmer or other computing device to a clinician who then confirms, denies, or modifies the new AV delay. Alternatively, the new BBA AV delay may be programmed by the clinician based on the identification of the preferred QRS COI.

In accordance with the process of FIG. 4A, the selecting operations selects the one of the candidate AV delays that manages delivery of pacing pulses at the LBB site at a point in time (fused) slightly before an intrinsic wave front is expected to propagate to or beyond a corresponding point along the right bundle branch.

CRT Pacing with LBB Electrode

Next, new and unique aspects herein are described in connection with an IMD configured to provide cardiac resynchronization therapy (CRT) utilizing an LBB electrode.

Figure 3B:
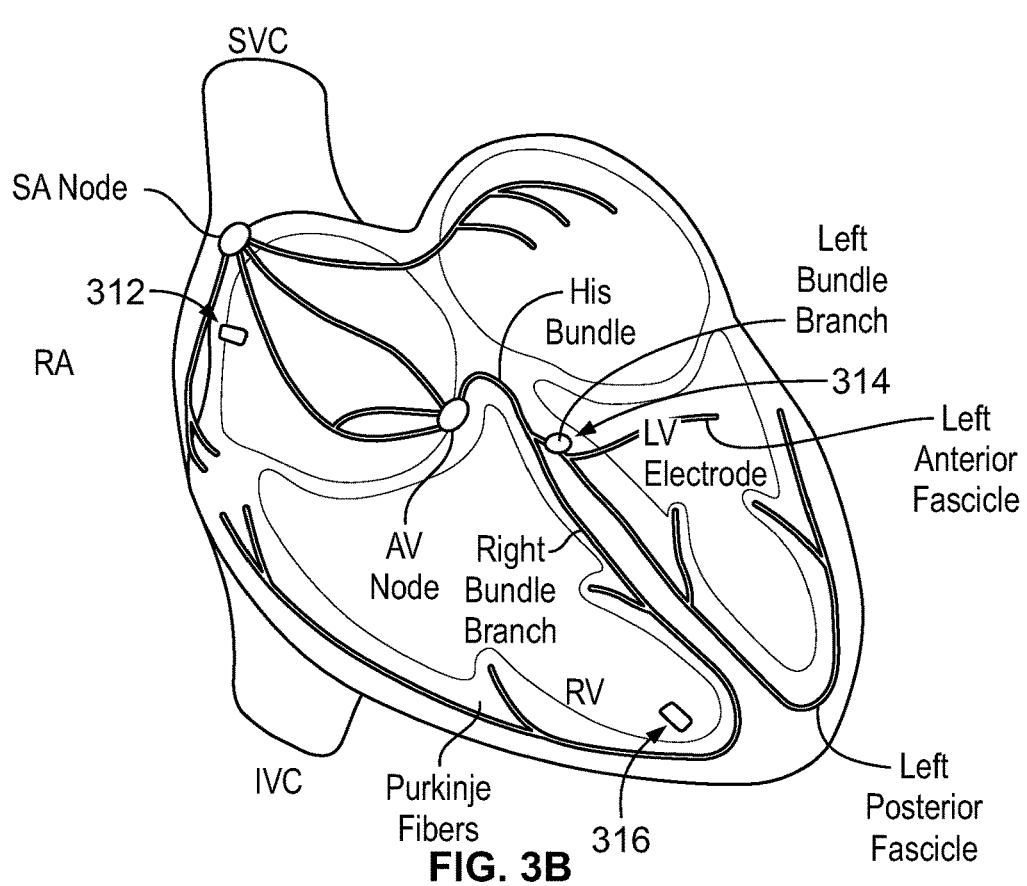
FIG. 3B illustrates a graphical representation of a heart with one or more electrodes located select pacing and sensing sites relative to the specialized conduction system in accordance with embodiments herein.

FIG. 3B illustrates a graphical representation of a heart with one or more electrodes located at select pacing and sensing sites relative to the specialized conduction system. A first electrode is located in the RA (e.g., proximate to the SA node), a second electrode is located at the RV apex and a third electrode is located in the septal wall to a depth proximate to the LBB in accordance with embodiments herein. For example, RA electrode 312 is located proximate to the SA node, RV electrode 316 is located at the RV apex and LBB electrode 314 is tunneled in the septal wall at a point and depth proximate to a proximal end of the LBB. The LBB electrode 314 is located distal to the HIS bundle such that a stimulus delivered at the LBB electrode 304 will induce an evoked response into a proximal portion of the LBB without substantially invoking an evoked response into the RBB.

The RA electrode 312 is connected through the corresponding RA lead to a contact located on an RA lead terminal at the proximal end of the lead. The RA lead terminal is plugged into an RA port of the header of the IMD. The RV electrode 316 is connected through the body of the corresponding RV lead to a contact located on an RV lead terminal at the proximal end of the RV lead. The RV lead terminal is plugged into an RV port at the header of the IMD. The LBB electrode 314 is connected through the body of the corresponding lead to a contact located on an LBB lead terminal at the proximal end of the lead. The LBB lead terminal is plugged into an LV port at a header of the IMD.

The IMD is generally configured to perform sensing and pacing functions based on the assumption that the RA, RV and LV ports are connected to leads having sensing and pacing electrodes located in the RA, proximate the RV apex and along the LV wall, respectively. Accordingly, the IMD normal operating parameters are set based in part on the assumption that CA signals sensed through a sensing channel, associated with the LV header port, represent CA signals sensed by one or more LV electrodes. The IMD is further generally configured to assume that stimulation delivered to the LV header port will be delivered through a lead to one or more electrodes located proximate the LV wall. However, in connection with the embodiment of FIG. 3B, the LV header port is connected to an electrode located at the proximal end of the LBB.

In accordance with new and unique aspects herein, embodiments are configured to manage sensing and pacing utilizing electrode 314 located at the proximal end of the LBB while coupled to the LV port in the header of the IMD.

Figure 4B:
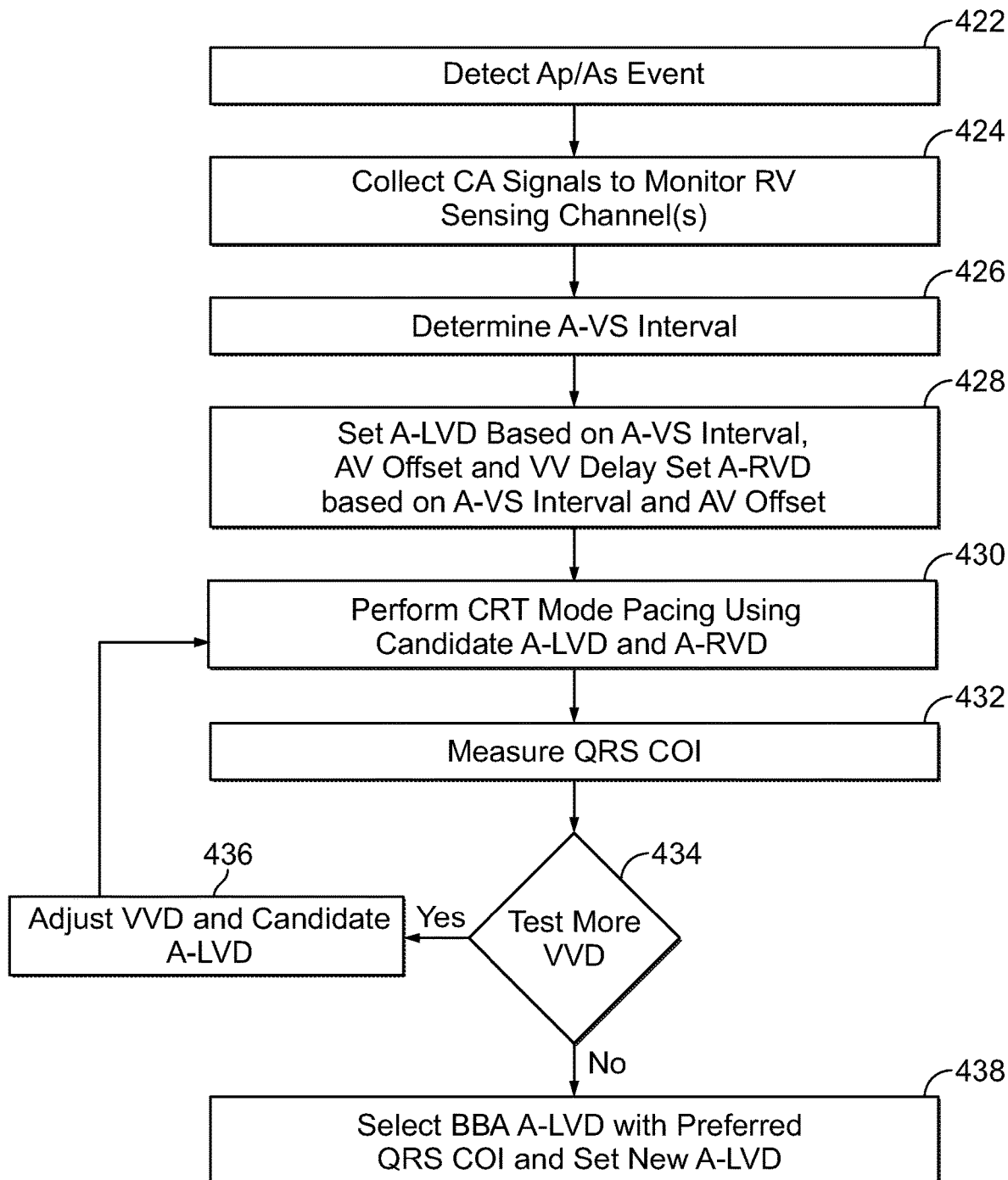
FIG. 4B illustrates a process for managing stimulation timing for the electrode configuration shown in FIG. 3B in accordance with embodiments herein.

FIG. 4B illustrates a process for managing sensing and stimulation timing for the electrode configuration shown in FIG. 3B in accordance with embodiments herein. In accordance with new and unique aspects herein, embodiments support connection of an LBB electrode to an LV header port while managing timing within the IMD to stimulate a proximal end of the left bundle branch at a point in time slightly after an intrinsic wave front propagates to or beyond a corresponding point along the right bundle branch. The IMD utilizes stimulation parameters associated with a "cardiac resynchronization therapy" or "CRT" mode for the IMD. In a conventional CRT mode, the IMD (and the AV delay management algorithm) are configured to time delivery of pacing pulses based in part on an assumption that an RV electrode is located at the RV apex and one or more LV electrodes are located along a lateral vein proximate to the LV posterior wall, the LV apex and other regions along the LV remote from the septal wall.

In accordance with new and unique aspects herein, embodiments modify a CRT therapy by placing an electrode at an LBB sensing/pacing site, instead of (and as a substitute for) an LV electrode located at a conventional LV pacing/sensing site. An LBB pacing site is utilized to encourage intrinsic propagation along the left anterior and left posterior fascicles, instead of (and as a substitute for) direct stimulation by an LV electrode along the LV posterior wall or LV apex.

At 422, the one or more processors detect a paced atrial (Ap) event or sensed atrial (As) event over an atrial sensing channel utilizing an RA electrode (e.g., 312 in FIG. 3B). When the paced or sensed atrial event is detected, one or more interval timers are started.

At 424, the one or more processors monitor an RV sensing channel for cardiac activity signals. The RV sensing channel utilizes a sensing vector that is defined in part by an electrode located at the RV apex or similar location (e.g., the electrode 316 in FIG. 3B). Given that the sensing vector utilizes an electrode located at the RV apex, a majority of the physical anatomy of the RV is in the near field of the sensing vector the CA signals from the RV sensing channel. The CA signals are analyzed to identify a right VS event. For example, in a bipolar sensing configuration, the sensing vector may extend between a combination of electrodes located on the lead that has the electrode located at the RV apex. As another example, in a monopolar sensing configuration, the sensing vector may extend between a can or housing of the IMD and the electrode at the RV apex. In both the monopolar and bipolar sensing configurations, a near field or primary portion of the sensing vector extends through the RV wall.

Optionally, at 424, the one or more processors may further monitor an LV sensing channel, associated with an LV header port, that is connected to the LBB electrode which defines the LV sensing vector.

At 426, the one or more processors determine an A-VS interval corresponding to the interval in time between the As or Ap event and the right Vs event.

At 428, the one or more processors set a candidate AV delay based on the AV interval and a bundle branch adjustment value. In connection with a CRT mode of operation and configuration for the IMD, the bundle branch adjustment value corresponds to a VV delay value and the candidate AV delay corresponds to a candidate A-LV delay. For example, the one or more processors may set the candidate A-LV delay based on the A-VS interval, an AV offset and a VV delay. For example, the AV offset may represent a preprogrammed period of time (e.g., in milliseconds), or a percentage. The VV delay may be preprogrammed or determined automatically. The initial A-VS interval, initial AV offset and initial VV delay may be determined and managed in accordance with the methods and systems described in U.S. Patent Application Publication 2012/0165892, titled "SYSTEMS AND METHODS FOR OPTIMZING AV/VV/PACING DELAYS USING COMBINED IEGM/IMPENDANCE-BASED TECHNIQUES FOR USE WITH IMPLANTABLE MEDICAL DEVICES" publication date Jun. 28, 2012; U.S. Patent Application Publication 2010/0145405, titled "SYSTEMS AND METHODS FOR CONTROLLING VENTRICULAR PACING IN PATIENTS WITH LONG INTER-ATRIAL CONDUCTION DELAYS" publication date Jun. 10, 2010; and U.S. Pat. No. 10,589,100, titled "METHOD AND DEVICE FOR PACING LATENCY BASED MULTI-POINT PACING" issue date Mar. 17, 2020, the complete subject matter of which are incorporated herein by reference in their entireties.

The VV delay represents a period of time a delay between timing of the LV and RV that is set to correct for bundle branch block. For example, the candidate A-LV delay may be set by subtracting a preprogrammed interval (corresponding to the AV offset) and by further subtracting a VV delay (e.g., A-LV delay=PR-AV offset-VV delay). As another example, the candidate A-LV delay may be set by reducing the A-VS interval by a percentage of time, as defined by the AV offset, and by further subtracting the VV delay.

The candidate A-LV delay, when set based on the A-VS interval, AV offset and VV delay, corresponds to the time interval between an A event and a VS event minus the HV interval, wherein the HV interval corresponds to the interval between an evoked response detected at the HIS bundle and detection of the VS event. In many instances, the HV interval is approximately equal to the programmed AV offset plus the VV delay.

Additionally, at 428, the one or more processors set an A-RV delay based on the A-VS interval and the AV offset. For example, the A-RV delay may be set by subtracting a preprogrammed interval (corresponding to the AV offset) and/or by reducing the A-VS interval by a percentage of time, as defined by the AV offset. By subtracting the VV delay from the A-VS interval, embodiments herein define the A-LV delay to be shorter than the A-RV delay, thereby causing the LV to be paced before the RV. In accordance with embodiments herein, the stimulus delivered in the RV may be set at a relatively small amplitude to achieve subthreshold RV pacing, such that the RV is not stimulated/captured by the pacing pulse delivered to the RV electrode. Alternatively, no stimulation pulses may be delivered to the RV electrode, but instead the RV electrode may be only used to measure VS events.

As a nonlimiting example, assume that the A-VS interval is 200 ms, the HV interval is 50 ms, the AV offset is programmed to 10 ms and the VV delay is programmed to 40 ms. The VV delay may be programmed in the foregoing manner to enable the LV electrode to pace before the RV experiences intrinsic conduction. Using the present nonlimiting examples of time intervals, the A-LV delay would be set to equal 150 ms (e.g., 200 ms-10 ms-40 ms), while the A-RV delay would be set to equal 190 ms (e.g., 200 ms-10 ms). The AV offset is utilized to account for changes in the A-VS interval by setting the A-LV delay to correspond to the A-VS interval minus the HV interval.

At 430, the one or more processors modify the parameters of the CRT mode implemented by the IMD to utilize the candidate A-LV delay and the A-RV delay.

At 432, the one or more processors manage the CRT mode of operation of the IMD utilizing the new candidate A-LV delay and A-RV delay for one or more cardiac beats. At 432, the one or more processors further measure a QRS COI. For example, the QRS COI may correspond to a duration of the QRS. As another example, the QRS COI may correspond to a morphology of the QRS. The operations at 430 and 432 may be implanted in connection with a single cardiac beat or a desired number of beats. For example, the one or more processors may utilize the candidate A-LV delay and A-RV delay in connection with an ensemble of beats (e.g., 5-10). The QRS COI may be separately measured for each of the beats within the ensemble, and then combined through a select mathematical combination (e.g., averaging) to form an ensemble QRS COI. Alternatively, the ensemble of beats may be combined through a select mathematical combination (e.g., averaging), and then the one or more processors determines the QRS COI for the ensemble.

At 434, the one or more processors determine whether to perform more testing of the candidate A-LV delays. When further testing is desirable, flow moves to 436 where the adjusting operation is repeated for multiple candidate BBA values that are chosen in an attempt to identify a time delivery of pacing pulses at the LBB site at a point in time fused with intrinsic waveform propagates to or beyond a corresponding point along the right bundle branch. A candidate AV delay is calculated in connection with each of the multiple BBA values.

At 436, the one or more processors adjust the VV delay and apply a corresponding adjustment/reset to the candidate A-LV delays. For example, the VV delay may be adjusted by incrementing or decrementing the value of the VV delay by predetermined stepped amounts. Each time the VV delay is adjusted during a corresponding iteration through 436, the candidate A-LV delay is recalculated, thereby similarly incrementing or decrementing the candidate A-LV delay by a corresponding stepped amount. For example, during a first iteration through 436, the VV delay may be increased by a select number of milliseconds, thereby decreasing the candidate AVD by the select number of milliseconds (e.g., 5 ms). Thereafter, flow returns to 430 and the operations at 430 and 432 are repeated utilizing the adjusted VV delay and candidate A-LV delay. The operations at 430-436 are iteratively repeated to obtain a collection of QRS COI for a corresponding collection of VV delays and candidate A-LV delays. For example, the QRS duration may be measured for 10 different VV delays, from which 5 VV delays represent 5 ms steps below the initial value utilized at 408, and from which 5 VV delays represent 5 ms steps above the initial value utilized at 408. Once a sufficient number of QRS COI are determined for incremental adjustments in the candidate A-LV delay, flow moves to 438.

At 438, the one or more processors review the QRS COI for the various corresponding adjustments in the candidate A-LV delays to identify a preferred QRS COI. For example, the preferred QRS COI may correspond to the narrowest QRS duration within the collection. As another example, the preferred QRS COI may correspond to an intermediate QRS duration within the collection. Additionally or alternatively, the QRS COI may correspond to a morphology of the QRS. As an example, a preferred QRS morphology may correspond to a maximum area under the curve for the QRS waveform, the QRS waveform exhibiting the largest peaks-valleys, the QRS waveform exhibiting a sharpest slope (e.g., maximum derivative) and the like.

At 438, a new BBA A-LV delay is set corresponding to an associated candidate A-LV delay based on the preferred QRS COI. The new BBA A-LV delay may be automatically set by the one or more processors. Alternatively, the new BBA A-LV delay may be presented on a GUI of programmer or other computing device to a clinician who then confirms, denies, or modifies the new BBA A-LV delay. Alternatively, the new BBA A-LV delay may be programmed by the clinician based on the identification of the preferred QRS COI.

CRT Pacing with HIS Electrode (LBBB Correction)

Next, new and unique aspects herein are described in connection with an IMD configured to provide cardiac resynchronization therapy (CRT) in connection with left bundle branch block utilizing a HIS electrode.

Figure 3C:
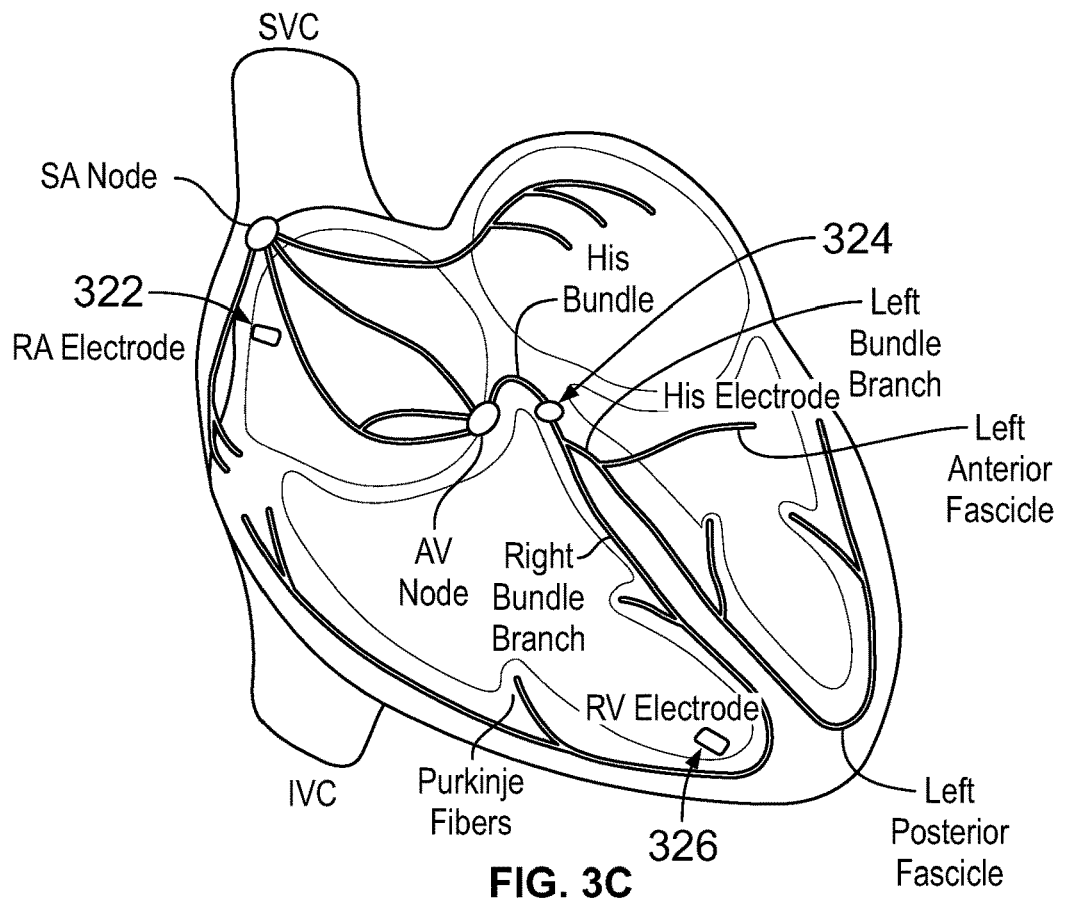
FIG. 3C illustrates a graphical representation of a heart with one or more electrodes located select pacing and sensing sites relative to the specialized conduction system in accordance with embodiments herein.

FIG. 3C illustrates a graphical representation of a heart with one or more electrodes located at select pacing and sensing sites relative to the specialized conduction system. A first electrode is located in the RA (e.g., proximate to the SA node), a second electrode is located at the RV apex and a third electrode is located proximate to the HIS bundle in accordance with embodiments herein. For example, RA electrode 322 is located proximate to the SA node, RV electrode 326 is located at the RV apex and HIS electrode 324 is located proximate to the HIS bundle upstream in the specialized conduction system from the left and right bundle branches. The HIS electrode 324 is such that a stimulus delivered at the HIS electrode 324 will induce an evoked response into the HIS bundle that will in turn propagate to the RBB and LBB.

The RA electrode 322 is connected through the corresponding RA lead to an RA lead terminal at the proximal end of the lead. The RA lead terminal is plugged into an RA header port of the header of the IMD. The RV electrode 326 is connected through the body of the corresponding RV lead to an RV lead terminal at the proximal end of the RV lead. The RV lead terminal is plugged into an RV header port of the IMD. The HIS electrode 324 is connected through the body of the corresponding lead to a HIS lead terminal at the proximal end of the lead. The HIS lead terminal is plugged into an LV header port of the IMD.

The IMD and the AV delay management algorithm are generally configured to perform sensing and pacing functions based on the assumption that the RA, RV and LV ports are connected to leads having sensing and pacing electrodes located at in the RA, proximate to the RV apex and along the LV wall, respectively. Accordingly, the IMD normal operating parameters and baseline AV delay management algorithm are set based in part on the assumption that CA signals sensed through a sensing channel, associated with the LV port, represent CA signals sensed by one or more LV electrodes located along the LV wall. The IMD is further generally configured to assume that stimulation delivered to the LV port will be delivered through a lead to one or more electrodes located proximate the LV wall. However, in connection with the embodiment of FIG. 3C, the LV header port is connected to an electrode located at the HIS bundle.

In accordance with new and unique aspects herein, embodiments are configured to manage sensing and pacing utilizing electrode 324 located at the HIS bundle while coupled to the LV header port of the IMD.

Figure 4C:
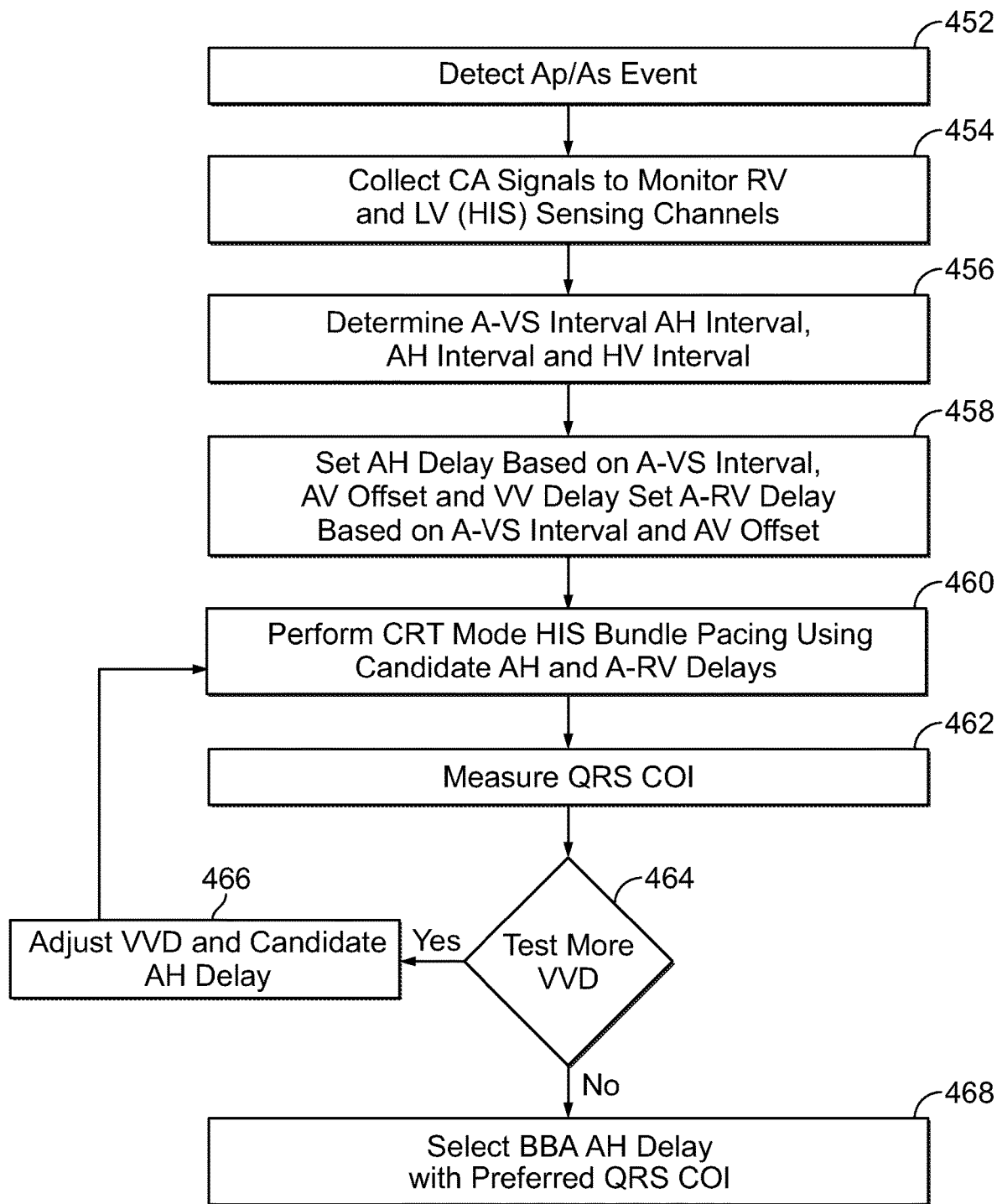
FIG. 4C illustrates a process for managing stimulation timing for the electrode configuration shown in FIG. 3C in accordance with embodiments herein.

FIG. 4C illustrates a process for managing sensing and stimulation timing for the electrode configuration shown in FIG. 3C in accordance with embodiments herein. In accordance with new and unique aspects herein, embodiments support connection of an HIS electrode to an LV header port while managing timing within the IMD to stimulate the HIS bundle to achieve substantially 100% HIS bundle capture with left bundle branch block correction. The IMD utilizes stimulation parameters associated with a "cardiac resynchronization therapy" or "CRT" mode for the IMD.

In accordance with new and unique aspects herein, embodiments modify a CRT therapy by placing an electrode at a HIS sensing/pacing site, instead of (and as a substitute for) an LV electrode located at a conventional LV pacing/sensing site. A HIS pacing site is utilized to encourage activation along the native left and right bundle branches, instead of (and as a substitute for) direct stimulation by an LV electrode along the LV posterior wall or LV apex.

At 452, the one or more processors detect a paced atrial (Ap) event or sensed atrial (As) event over an atrial sensing channel utilizing an RA electrode (e.g., 322 in FIG. 3C). When the paced or sensed atrial event is detected, one or more interval timers are started.

At 454, the one or more processors monitor LV and RV sensing channels for cardiac activity signals. The RV sensing channel collect CA signals along a sensing vector that is defined in part by an electrode located at the RV apex or similar location (e.g., the electrode 326 in FIG. 3C). The RV sensing channel may utilize a bipolar or monopolar sensing configuration.

At 454, the one or more processors also monitor an LV sensing channel that receives CA signals incoming through the LV header port. As noted above, the LV header port is connected to a HIS electrode and thus the CA signals received over the LV sensing channel are collected along a sensing vector extending through the HIS bundle, and not through a majority of the LV wall.

At 456, the one or more processors determine an A-VS interval corresponding to the interval in time between the As or Ap event and the right Vs event. At 456, the one or more processors also determine an atrial sensed/paced to HIS sensed (AH) interval corresponding to the interval between the As or Ap event and HIS evoked response. Additionally or alternatively, the one or more processors may also determine a time between the HIS evoked response and the right VS event (HV) interval. The HV interval corresponds to the time between the HIS evoked response and onset of a QRS complex.

At 458, the one or more processors set a candidate AV delay based on the AV interval, AV offset and a bundle branch adjustment value. In connection with a CRT mode of operation and configuration for the IMD, the bundle branch adjustment value corresponds to a VV delay value and the candidate AV delay corresponds to a candidate A-LV (HIS) delay, also referred to as a candidate AH delay. The candidate AH delay is also referred to as a candidate A-LV (HIS) delay given that the HIS electrode is connected to the LV header port. The candidate AV delay corresponds to a candidate AH delay following a new As or Ap event before a pacing stimulus is delivered through the LV header port to the HIS site.

For example, the one or more processors may set the candidate AH delay based on the A-VS interval, an AV offset and a VV delay to form the candidate AH delay. For example, the AV offset may represent a preprogrammed period of time (e.g., in milliseconds), or a percentage. The VV delay may be preprogrammed by a clinician and/or automatically determined. For example, the VV delay may be set to represent a value that is less than the HV interval to avoid detecting HIS bundle paced induced RV activation on the RV lead. In other words, only intrinsic RV activation would be detected on the RV lead when the VV delay is shorter than the HV interval.

For example, the candidate AH delay may be set by subtracting a preprogrammed interval (corresponding to the AV offset) and by further subtracting the VV delay (e.g., AH delay=PR—AV offset-VV delay). As another example, the candidate AH delay may be set by reducing the A-VS interval by a percentage of time, as defined by the AV offset, and by further subtracting the VV delay. The sum of the AV offset and the VV delay should be set to be greater than the HV interval to pace the HIS bundle before intrinsic HIS activation occurs.

Additionally, at 458, the one or more processors set an A-RV delay based on the A-VS interval and the AV offset. For example, the A-RV delay may be set by subtracting a preprogrammed interval (corresponding to the AV offset) and/or by reducing the AH interval by a percentage of time, as defined by the AV offset. By subtracting the VV delay from the A-RV interval, embodiments herein define the AH delay to be shorter than the A-RV delay, thereby causing the HIS to be paced before the RV. When intrinsic RV activation is detected on the RV lead, the AV offset can be utilized to automatically adjust the A-LV and A-RV delays according to RA-RV conduction time to regain preemptive HIS pacing. When intrinsic RV activation is detected on the RV lead, a new RA to RV conduction time is obtained and is used to calculate a new A-LV delay, which will be applied for subsequent beats to regain preemptive HIS pacing. For example, the methods, systems and devices described in the in U.S. Patent Application Publication 2012/0165892; U.S. Patent Application Publication 2010/0145405; U.S. Pat. No. 10,589,100, as well as any other patent or application references herein, may be utilized to automatically adjust the A-LV and A-RV delays Additionally or alternatively, the RV lead can be utilized for backup pacing in pacemaker-dependent patients or set to subthreshold pacing in patients with normal AV conduction. Subthreshold pacing is a method of setting the pacing amplitude and pulse width to the minimal values allowed by the device to conserve battery longevity. This is done when the CRT devices pacing, via an RV lead, cannot be turned off when LV (HIS lead) pacing is on.

As a nonlimiting example, assume that the AH interval is 150 ms and the HV interval is 50 ms for a total AV interval of 200 ms. The programmed AV offset may be set to 20 ms and the VV delay may be set to 40 ms (e.g., preprogrammed or based on the measured AH and HV intervals). Using the present nonlimiting examples of time intervals, the AH delay would be set to equal 140 ms (e.g., 200 ms−20 ms−40 ms), while the A-RV delay would be set to equal 180 ms (e.g., 200 ms−20 ms). The VV delay is programmed to a value less than the patient HV interval to avoid sensing HIS bundle pacing-induced RV activation. The AV offset plus the VV delay equal 60 ms (in the foregoing example) which is longer than the HV interval to ensure pacing of the HIS before the intrinsic HIS activation.

At 460, the one or more processors modify the parameters of the CRT mode implemented by the IMD to utilize the candidate AH delay and the A-RV delay while delivering HIS bundle pacing (HBP).

At 462, the one or more processors manage the CRT mode of operation of the IMD utilizing the new candidate AH delay and A-RV delay during HBP for one or more cardiac beats. At 462, the one or more processors further measure a QRS COI. For example, the QRS COI may correspond to a duration of the QRS complex. As another example, the QRS COI may correspond to a morphology of the QRS complex. The operations at 460 and 462 may be implemented in connection with a single cardiac beat or a desired number of beats. For example, the one or more processors may utilize the candidate AH delay and A-RV delay in connection with HBP for an ensemble of beats (e.g., 5-10). The QRS COI may be separately measured for each of the beats within the ensemble, and then combined through a select mathematical combination (e.g., averaging) to form an ensemble QRS COI. Alternatively, the ensemble of beats may be combined through a select mathematical combination (e.g., averaging), and then the one or more processors determines the QRS COI for the ensemble.

At 464, the one or more processors determine whether to perform more testing of HBP with alternative VV delays and corresponding candidate AH delays. When further testing is desirable, flow moves to 466.

At 466, the one or more processors adjust the VV delay and apply a corresponding adjustment to the candidate AH delay. For example, the VV delay may be adjusted by incrementing or decrementing the value of the VV delay by predetermined stepped amounts. Each time the VV delay is adjusted during a corresponding iteration through 466, the candidate AH delay (also referred to as the candidate A-LV (his) delay) is recalculated and similarly adjusted by incrementing or decrementing the candidate AH delay by a corresponding stepped amount. For example, during a first iteration through 466, the VV delay may be increased by a select number of milliseconds, thereby decreasing the candidate AH delay by the select number of milliseconds (e.g., 5 ms). Thereafter, flow returns to 460 and the operations at 460 and 462 are repeated utilizing the adjusted VV delay and candidate AH delay. The operations at 460-466 are iteratively repeated to obtain a collection of QRS COI for a corresponding collection of VV delays and AH delays. For example, the QRS duration may be measured for 10 different VV delays, from which 5 VV delays represent 5 ms steps below the initial value utilized at 458, and from which 5 VV delays represent 5 ms steps above the initial value utilized at 458. Once a sufficient number of QRS COI are determined for incremental adjustments in the candidate AH delay, flow moves to 468.

At 468, the one or more processors review the QRS COI for the various corresponding adjustments in the candidate AH delays to identify a preferred QRS COI. For example, the preferred QRS COI may correspond to the narrowest QRS duration within the collection. As another example, the preferred QRS COI may correspond to an intermediate QRS duration within the collection. Additionally or alternatively, the QRS COI may correspond to a morphology of the QRS. As an example, a preferred QRS morphology may correspond to a maximum area under the curve for the QRS waveform, the QRS waveform exhibiting the largest peaks-valleys, the QRS waveform exhibiting a sharpest slope (e.g., maximum derivative) and the like.

At 468, a new BBA AH delay is set corresponding to an associated BBA AH delay based on the preferred QRS COI. The BBA AH delay corresponding to a BBA A-LV (HIS) delay representing a delay following a new As or Ap event before a pacing stimulus is delivered through the LV header port to the HIS site. The new BBA AH delay may be automatically set by the one or more processors. Alternatively, the new BBA AH delay may be presented on a GUI of programmer or other computing device to a clinician who then confirms, denies, or modifies the new BBA AH delay. Alternatively, the new BBA AH delay may be programmed by the clinician based on the identification of the preferred QRS COI.

Optionally, the configuration of FIGS. 3C and 4C may be implemented while adjusting the combination of header ports to which the various leads/electrodes are connected. For example, an alternative configuration, HIS bundle pacing may be implemented to achieve LBBB correction while connecting the RA lead to the RA header port, the RV lead to the LV header port and the HIS lead to the RV header port. In the foregoing alternative configuration, the connections for the RV lead and the HIS lead have been switched at the IMD header from the discussion above in connection with FIGS. 3C and 4C. In the alternative configuration with the RV lead connected to the LV port and the HIS lead connected to the RV port, the process of FIG. 4C is repeated with the following adjustments. At 458, the one or more processors set in A-LV (RV lead) delay to subtract, from the A-VS interval, the AV offset and the VV delay, provided that the VV delay is a negative value to achieve pacing first at an RV header port (his lead). At 458, the one or more processors calculate the A-RV (his lead) delay by subtracting the AV offset from the A-VS interval. The AV offset is programmed to be greater than the HV interval in order to pace the HIS before intrinsic HIS activation occurs. When intrinsic ventricular activation is detected in the HIS lead through the RV header port, the AV offset is automatically adjusted to adjust the A-LV delay and A-RV delay relative to one another, according to an RA-V conduction time to regain preemptive HIS pacing.

Optionally, the RV lead may be utilized for backup pacing in pacemaker—dependent patients or set to subthreshold pacing in patients with normal AV conduction.

CRT Pacing with HIS Electrode (No LBBB Correction)

Next, new and unique aspects herein are described in connection with an IMD configured to provide cardiac resynchronization therapy (CRT) in connection with HIS bundle pacing, but when LBBB correction cannot be obtained.

Figure 3D:
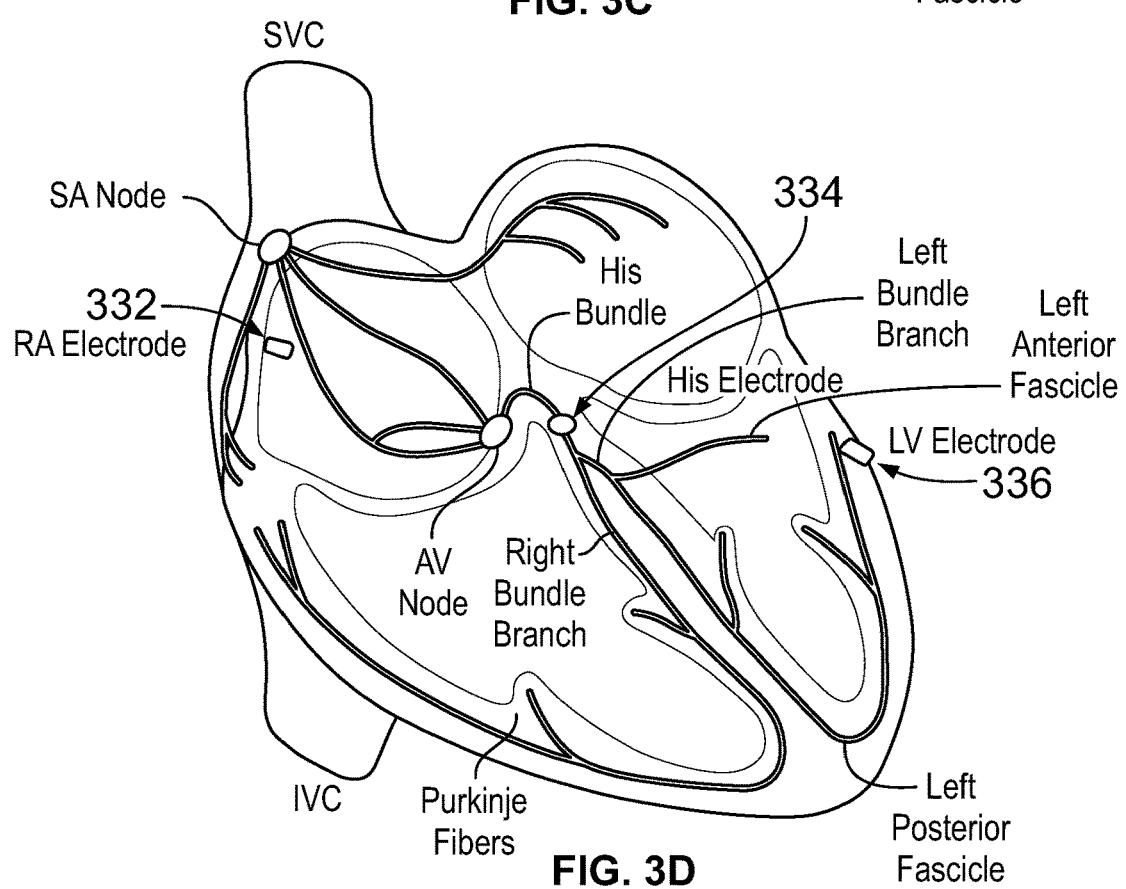
FIG. 3D illustrates a graphical representation of a heart with one or more electrodes located select pacing and sensing sites relative to the specialized conduction system in accordance with embodiments herein.

FIG. 3D illustrates a graphical representation of a heart with one or more electrodes located at select pacing and sensing sites relative to the specialized conduction system. A first electrode is located in the RA (e.g., proximate to the SA node), a second electrode is located along the LV wall and a third electrode is located proximate to the HIS bundle in accordance with embodiments herein. For example, RA electrode 332 is located proximate to the SA node, LV electrode 336 is located along the LV wall and HIS electrode 334 is located proximate to the HIS bundle upstream in the specialized conduction system from the left and right bundle branches. The HIS electrode 334 is such that a stimulus delivered at the HIS electrode 324 will induce an evoked response into the HIS bundle that will in turn propagate to the RBB and LBB. While only a single LV electrode 336 as illustrated, it is recognized that multiple LV electrodes may be provided along the LV wall, such as in connection with providing multipoint LV pacing.

The RA electrode 332 is connected through the corresponding RA lead to an RA lead terminal at the proximal end of the lead. The RA lead terminal is plugged into an RA header port of the header of the IMD. The LV electrode 336 is connected through the body of the corresponding LV lead to an LV lead terminal at the proximal end of the LV lead. The LV lead terminal is plugged into an LV header port of the IMD. The HIS electrode 334 is connected through the body of the corresponding lead to a HIS lead terminal at the proximal end of the lead. The HIS lead terminal is plugged into an RV header port of the IMD.

The IMD and the AV delay management algorithm are generally configured to perform sensing and pacing functions based on the assumption that the RA, RV and LV ports are connected to leads having sensing and pacing electrodes located at in the RA, proximate to the RV apex and along the LV wall, respectively. However, as illustrated in FIG. 3-D, the RV header port is connected to an electrode located proximate the HIS, not the RV apex. The IMD normal operating parameters and baseline AV delay management algorithm are set based in part on the assumption that CA signals sensed through a sensing channel, associated with the RV port, represent CA signals sensed by one or more RV electrodes located proximate the apex of the RV, however in the present embodiment, the RV header port is connected to an electrode located proximate the HIS. The IMD is further generally configured to assume that stimulation delivered to the RV port will be delivered through a lead to one or more electrodes located proximate the RV apex. However, in connection with the embodiment of FIG. 3D, the RV header port is connected to an electrode located at the HIS bundle.

In accordance with new and unique aspects herein, embodiments are configured to manage sensing and pacing utilizing electrode 334 located at the HIS bundle while coupled to the RV header port of the IMD.

Figure 4D:
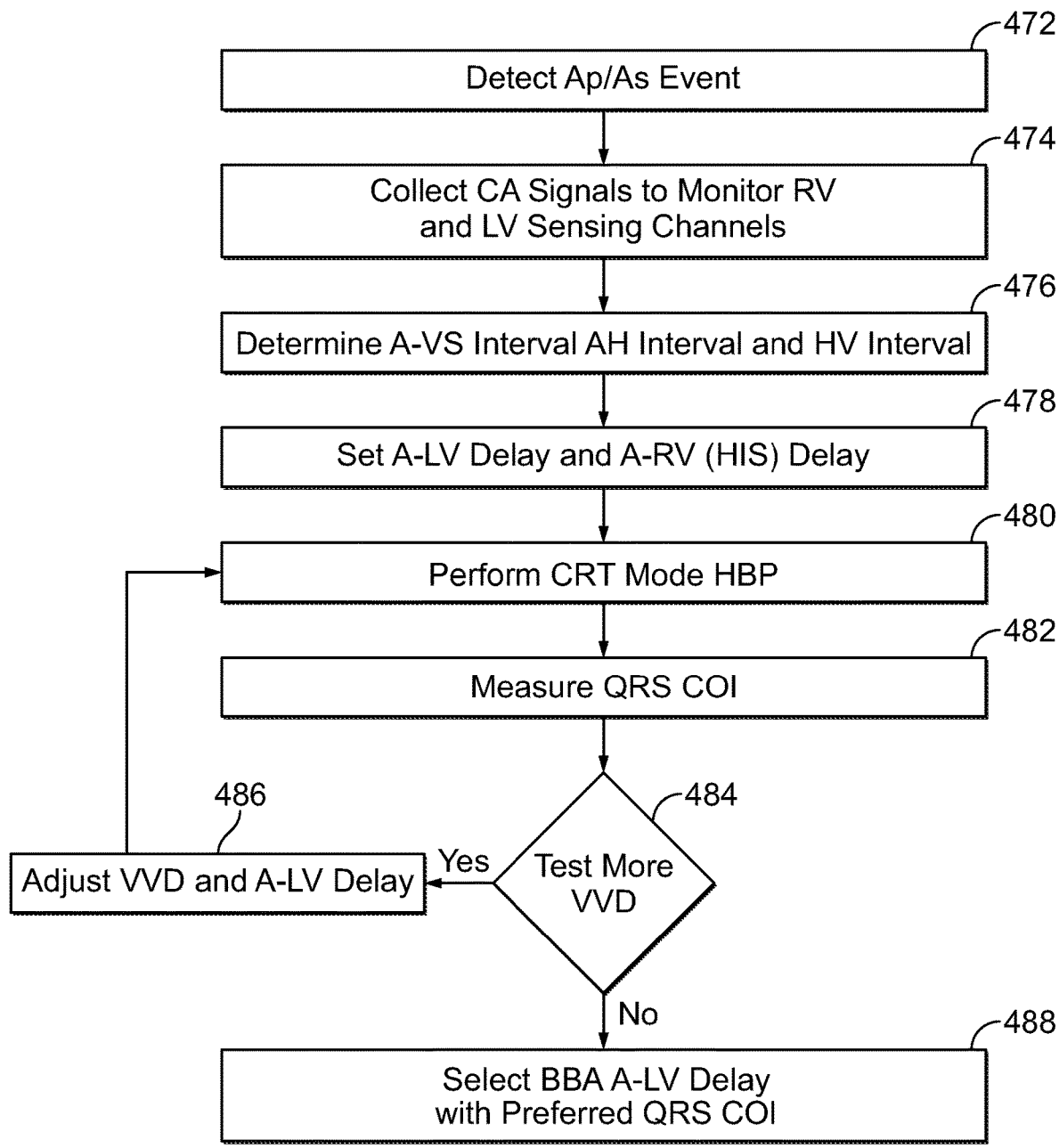
FIG. 4D illustrates a process for managing stimulation timing for the electrode configuration shown in FIG. 3D in accordance with embodiments herein.

FIG. 4D illustrates a process for managing sensing and stimulation timing for the electrode configuration shown in FIG. 3D in accordance with embodiments herein. In accordance with new and unique aspects herein, embodiments support connection of an HIS electrode to an RV header port while managing timing within the IMD to stimulate the HIS bundle to achieve substantially 100% HIS bundle capture with left bundle branch block correction. The IMD utilizes stimulation parameters associated with a "cardiac resynchronization therapy" or "CRT" mode for the IMD.

In accordance with new and unique aspects herein, embodiments modify a CRT therapy by placing an electrode at a HIS sensing/pacing site, instead of (and as a substitute for) an RV electrode located at a conventional RV pacing/sensing site. A HIS pacing site is utilized to encourage intrinsic propagation along the left and right bundle branches, instead of an as a substitute for direct stimulation by an RV electrode at the RV apex.

At 472, the one or more processors detect a paced atrial (Ap) event or sensed atrial (As) event over an atrial sensing channel utilizing an RA electrode (e.g., 332 in FIG. 3D). When the paced or sensed atrial event is detected, one or more interval timers are started.

At 474, the one or more processors monitor LV and RV sensing channels for cardiac activity signals. The LV sensing channel utilizes a sensing vector that is defined in part by an electrode located along the LV wall (electrode 336 in FIG. 3D), while the RV sensing channel utilizes a sensing vector that is defined in part by an electrode located at the HIS bundle (electrode 334). The LV and/or RV sensing channels may utilize bipolar or monopolar sensing configurations.

The RV sensing channel utilizes a sensing vector that is defined in part by an electrode located at the HIS bundle. Given that the sensing vector utilizes an electrode located at the HIS, a majority of the physical anatomy of the RV is somewhat tangential to the sensing vector. For example, in a bipolar sensing configuration, the sensing vector may extend between a combination of electrodes located on the lead that has the electrode located at the HIS. As another example, in a monopolar sensing configuration, the sensing vector may extend between a can or housing of the IMD and the electrode at the HIS. In both the monopolar and bipolar sensing configurations, a near field or primary portion of the sensing vector is located at the HIS, while an apex of the RV is more distant from the sensing vector and may be considered to be in a midfield or secondary portion the sensing vector.

The CA signals collected over the RV (HIS) sensing channel include a first signal component associated with the near field, such as evoked responses experienced at the HIS. The HIS evoked response is directly measured from the CA signals and utilized to calculate an AH interval between the paced or sensed atrial event and the evoked response occurring at the HIS. The CA signals will also include a second signal component associated with the midfield, such as ventricular (Vs) events. A VS event represents a depolarization signal experienced when the RV contracts and will represent a substantially larger signal than the first signal component corresponding to the evoked response at the HIS, even though a majority of the RV muscle is spaced a midfield distance from a center of the sensing vector.

Optionally, separate sensing channels may be utilized to collect CA signals associated with the first and second signal components.

At 474, the one or more processors identify the separate first and second signal components, associated with the HIS and the VS event, respectively. The first and second signal components maybe identified by the one or more processors, while executing program instructions to analyze digitize CA signals. Additionally or alternatively, the first and second signal components maybe identified by the one or more processors based on a flag or other signal generated by firmware or hardware. For example, firmware or hardware may identify the HIS evoked response and VS event, respectively, when an amplitude of the CA signals exceeds first and second thresholds within a HIS evoked response search window and a VS event search window, respectively. The HIS and VS search windows are set at predetermined periods of time following the As/Ap event.

At 476, the one or more processors determine an A-VS interval corresponding to the interval in time between the As or Ap event and the right Vs event (as identified from the second signal component of the CA signal sensed over the HIS sensing vector, corresponding to the RV sensing channel). At 476, the one or more processors also determine an atrial sensed/paced to HIS sensed (AH) interval corresponding to the interval between the time between the As or Ap event and the HIS evoked response. Additionally or alternatively, the one or more processors may also determine time between the HIS evoked response and the right VS event (HV) interval. The HV interval corresponds to the time between the HIS evoked response and onset of a QRS complex, both signal components of which are detected over the HIS sensing vector.

At 478, the one or more processors set a candidate AV delay based on the AV interval, AV offset and a bundle branch adjustment value. In connection with a CRT mode of operation and configuration for the IMD, the bundle branch adjustment value corresponds to a VV delay value and the candidate AV delay corresponds to a candidate A-LV delay. The candidate A-LV delay is utilized in connection with timing pacing pulses delivered to the one or more LV electrodes located along the LV wall. For example, the AV offset may represent a preprogrammed period of time (e.g., in milliseconds), or a percentage. The VV delay may be preprogrammed by a clinician and/or automatically determined. The VV delay is set to represent a negative value (e.g., −50 ms) given that the first ventricular pacing pulse is to be delivered from the HIS electrode into the bundle of HIS (where the HIS electrode is connected to the RV header port) and not from an LV electrode located along the LV wall. For example, the VV delay may be initially programmed to the HV interval minus a predetermined amount (e.g., 10 ms). As explained hereafter, the VV delay is incrementally adjusted until a preferred QRS COI is obtained.

As explained herein, the AV offset is generally set to be greater than the HV interval in order to pace the HIS before intrinsic HIS activation occurs. The A-VS interval measured over the HIS sensing vector (RV sensing channel) is utilized to adjust the AV offset automatically, thereby automatically adjusting the A-RV/LV delay to achieve physiologic pacing between the HIS pacing site and the LV pacing site.

For example, the candidate A-LV delay may be set by subtracting a preprogrammed interval (corresponding to the AV offset) and by further subtracting the (negative) VV delay (e.g., A-LV delay=PR—AV offset-(negative VV delay)). As another example, the candidate A-LV delay may be set by reducing the A-VS interval by a percentage of time, as defined by the AV offset, and by further subtracting the negative VV delay.

Additionally, at 478, the one or more processors set an A-RV (HIS) delay based on the A-VS interval and the AV offset. For example, the A-RV (HIS) delay may be set by subtracting a preprogrammed interval (corresponding to the AV offset) and/or by reducing the A-VS interval by a percentage of time, as defined by the AV offset.

Additionally or alternatively, the RV lead can be utilized for backup pacing in pacemaker-dependent patients or set to subthreshold pacing in patients with normal AV conduction.

As a nonlimiting example, assume that the AH interval is 150 ms and the HV interval is 50 ms for a total AV interval of 200 ms. The programmed AV offset may be set to 60 ms and the VV delay may be set to −50 ms (e.g., preprogrammed or based on the measured AH and HV intervals). Using the present nonlimiting examples of time intervals, the A-LV delay would be set to equal 190 ms (e.g., 200 ms−60 ms−(−50 ms)), while the A-RV delay would be set to equal 140 ms (e.g., 200 ms−60 ms). The VV delay is programmed to a value less than the patient HV interval to achieve HIS first pacing (through the RV header port) and to achieve physiologic (e.g., optimized) pacing at the HIS pacing site and the LV pacing site. The AV offset is programmed to a value greater than the HV interval to pace the HIS before and intrinsic HIS activation occurs.

At 480, the one or more processors modify the parameters of the CRT mode implemented by the IMD to utilize the candidate A-LV delay and the A-RV delay while delivering HIS bundle pacing (HBP).

At 482, the one or more processors manage the CRT mode of operation of the IMD utilizing the new candidate A-LV delay and A-RV delay during HBP for one or more cardiac beats. At 482, the one or more processors further measure a QRS COI. For example, the QRS COI may correspond to a duration of the QRS complex. As another example, the QRS COI may correspond to a morphology of the QRS complex. The operations at 480 and 482 may be implemented in connection with a single cardiac beat or a desired number of beats. For example, the one or more processors may utilize the candidate A-LV delay and A-RV delay in connection with HBP for an ensemble of beats (e.g., 5-10). The QRS COI may be separately measured for each of the beats within the ensemble, and then combined through a select mathematical combination (e.g., averaging) to form an ensemble QRS COI. Alternatively, the ensemble of beats may be combined through a select mathematical combination (e.g., averaging), and then the one or more processors determines the QRS COI for the ensemble.

At 484, the one or more processors determine whether to perform more testing of HBP with alternative VV delays and corresponding candidate A-LV delays. When further testing is desirable, flow moves to 486.

At 486, the one or more processors adjust the VV delay and apply a corresponding adjustment to the candidate AH delay. For example, the VV delay may be adjusted by incrementing or decrementing the value of the VV delay by predetermined stepped amounts. Each time the VV delay is adjusted during a corresponding iteration through 486, the candidate A-LV delay is recalculated and similarly adjusted by incrementing or decrementing the candidate A-LV delay by a corresponding stepped amount. For example, during a first iteration through 486, the VV delay may be increased by a select number of milliseconds, thereby decreasing the candidate A-LV delay by the select number of milliseconds (e.g., 5 ms). Thereafter, flow returns to 480 and the operations at 480 and 482 are repeated utilizing the adjusted VV delay and candidate A-LV delay. The operations at 480-486 are iteratively repeated to obtain a collection of QRS COI for a corresponding collection of VV delays and candidate A-LV delays. For example, the QRS duration may be measured for 10 different VV delays, from which 5 VV delays represent 5 ms steps below the initial value utilized at 478, and from which 5 VV delays represent 5 ms steps above the initial value utilized at 478. Once a sufficient number of QRS COI are determined for incremental adjustments in the candidate A-LV delay, flow moves to 488.

At 488, the one or more processors review the QRS COI for the various corresponding adjustments in the candidate A-LV delays to identify a preferred QRS COI. For example, the preferred QRS COI may correspond to the narrowest QRS duration within the collection. As another example, the preferred QRS COI may correspond to an intermediate QRS duration within the collection. Additionally or alternatively, the QRS COI may correspond to a morphology of the QRS. As an example, a preferred QRS morphology may correspond to a maximum area under the curve for the QRS waveform, the QRS waveform exhibiting the largest peaks-valleys, the QRS waveform exhibiting a sharpest slope (e.g., maximum derivative) and the like.

At 488, a new BBA A-LV delay is set corresponding to an associated candidate A-LV delay based on the preferred QRS COI. The new BBA A-LV delay may be automatically set by the one or more processors. Alternatively, the new BBA A-LV delay may be presented on a GUI of programmer or other computing device to a clinician who then confirms, denies, or modifies the new BBA A-LV delay. Alternatively, the new BBA A-LV delay may be programmed by the clinician based on the identification of the preferred QRS COI.

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A system for managing atrial-ventricular (AV) delay adjustments, the system comprising:
    an implantable medical device (IMD) having a header that includes a right atrial (RA) header port, a right ventricular (RV) header port and a left ventricular (LV) header port;
    a first lead having a first electrode configured to be located proximate to an atrial (A) site, the first lead having a proximal end with a first lead terminal connected to the RA header port; and
    a second lead having a second electrode configured to be located proximate to at least one of a left bundle branch (LBB) site or a HIS bundle, the second lead having a proximal end with a second lead terminal connected to the RV or LV header port,
    memory configured to store program instructions;
    one or more processors that, when configured to execute the program instructions:
    measure an AV interval corresponding to an interval between Lan atrial paced (Ap) event or an atrial sensed (As) event, paced or sensed at the first electrode, and La sensed ventricular (Vs) event sensed at the second electrode;
    set a candidate AV delay based on the AV interval and based on a bundle branch adjustment (BBA) value, wherein the BBA value represents an adjustment to the AV interval to account for sensing the Vs event at the second electrode which is located proximate to at least one of the LBB site or the HIS bundle but connected to the RV or LV header port;
    measure a QRS characteristic of interest (COI) while utilizing the candidate AV delay in connection with delivering a pacing therapy by the IMD;
    adjust the BBA value and reset the candidate AV delay based on the AV interval and the BBA value as adjusted;
    repeat the adjust, reset and measure to obtain a collection of QRS COIs and corresponding candidate AV delays;
    select one of the candidate AV delays, that corresponds to a select one of the QRS COIs, as a BBA AV delay; and
    manage the pacing therapy, utilized by the IMD, based on the BBA AV delay.

2. The system of claim 1, wherein the one or more processors are configured, when executing the program instructions, to implement, as the pacing therapy, a DDD mode pacing therapy, wherein the second electrode represents an LBB electrode configured to be implanted through a septal wall to a depth sufficient to be located proximate to the LBB site, the second lead terminal configured to connect the LBB electrode to the RV header port; and
    the IMD further comprising sensing circuitry configured to sense cardiac activity (CA) signals over an RV sensing channel, associated with the RV header port, wherein the CA signals are collected along a sensing vector defined at least in part by the LBB electrode,
    wherein the measure, adjust, repeat and select operations are based in part on the CA signals.

3. The system of claim 1, wherein the one or more processors are further configured to select the one of the candidate AV delays that manages delivery of pacing pulses at the LBB site at a select point in time before an intrinsic wave front is expected to propagate to or beyond a corresponding point along a right bundle branch.

4. The system of claim 1, wherein the one or more processors are further configured to select the one of the candidate AV delays that resulted in a narrowest QRS duration within the collection of QRS COIs.

5. The system of claim 1, wherein the one or more processors are further configured to repeatedly adjust the candidate AV delay by subtracting, from the AV interval, multiple candidate BBA values in order to time delivery of pacing pulses at the LBB site at a point in time fused with intrinsic waveform propagation to or beyond a corresponding point along a right bundle branch.

6. The system of claim 1, wherein the second electrode represents an LBB electrode configured to be implanted through a septal wall to a depth sufficient to be located proximate to the LBB site, the second lead terminal configured to connect the LBB electrode to the LV header port, wherein the pacing therapy corresponds to a cardiac resynchronization therapy (CRT) pacing therapy configured to deliver pacing pulses through the LV header port of the IMD to the LBB electrode.

7. The system of claim 6, wherein the one or more processors are further configured to select the one of the candidate AV delays that manages delivery of pacing pulses at the LBB site at a select point in time after an intrinsic wave front is expected to propagate to or beyond a corresponding point along a right bundle branch.

8. The system of claim 1,
    wherein the second electrode represents a load including a HIS electrode configured to be located at the HIS bundle, the lead including a proximal terminal configured to connect the HIS electrode to the RV header port;
    the IMD further comprising:
    sensing circuit configured to sense cardiac activity (CA) signals over an RV sensing channel associated with the RV header port, wherein the CA signals are collected along a sensing vector defined at least in part by the HIS electrode, the candidate AV delays and BBA AV delays following a new As or Ap event before a pacing stimulus is delivered through the RV header port to the HIS bundle.

9. The system of claim 1, wherein the BBA value provides an adjustment to the AV interval to account for the Vs event being sensed at the second electrode when connected to the RV header port and located proximate to at least one of the LBB site or the HIS bundle.

10. The system of claim 1, wherein the BBA value provides an adjustment to the AV interval to account for the Vs event being sensed at the second electrode when configured to be located proximate to the LBB site and the second lead terminal is connected to the RV header port.

11. The system of claim 1, wherein the second electrode is configured to be located proximate to the HIS bundle and the second lead terminal is connected to the RV header port, the system further comprising a third lead having a third electrode configured to be located proximate to the LV and having a third lead terminal connected to the LV header port.

12. The system of claim 1, wherein the second electrode is configured to be located proximate to the HIS bundle and the second lead terminal is connected to the LV header port, the system further comprising a third lead having a third electrode configured to be located proximate to a right ventricular (RV) apex and having a third lead terminal connected to the RV header port.

13. A system for managing atrial-ventricular (AV) delay adjustments, the system comprising:
electrodes configured to be located proximate to an atrial (A) site and at least one of a left bundle branch (LBB) site or a HIS bundle;
an implantable medical device (IMD) having a header that includes a right atrial (RA) header port, a right ventricular (RV) header port and a left ventricular (LV) header port;
memory configured to store program instructions;
one or more processors that, when configured to execute the program instructions:
measure an AV interval corresponding to an interval between an atrial paced (Ap) event or an atrial sensed (As) event and a sensed ventricular (Vs) event;
set a candidate AV delay based on the AV interval and a bundle branch adjustment (BBA) value;
measure a QRS characteristic of interest (COI) while utilizing the candidate AV delay in connection with delivering a pacing therapy by the IMD;
adjust the BBA value and reset the candidate AV delay based on the BBA value as adjusted;
repeat the adjust, reset and measure to obtain a collection of QRS COIs and corresponding candidate AV delays;
select one of the candidate AV delays, that corresponds to a select one of the QRS COIs, as a BBA AV delay; and
manage the pacing therapy, utilized by the IMD, based on the BBA AV delay,
wherein the one or more processors are further configured to set, as the candidate AV delay, a candidate A-LV delay by adjusting the AV interval based on an AV offset and further subtracting a VV delay from the AV interval, the VV delay corresponding to the BBA value, the adjusting further comprising utilizing multiple candidate BBA values in order to time delivery of pacing pulses at the LBB site at a point in time fused with intrinsic waveform propagation to or beyond a corresponding point along a right bundle branch.

14. A system for managing atrial-ventricular (AV) delay adjustments, the system comprising:
an implantable medical device (IMD) having a header that includes a right atrial (RA) header port, a right ventricular (RV) header port and a left ventricular (LV) header port;
a first lead having a first electrode configured to be located proximate to an atrial (A) site, the first lead having a proximal end with a first lead terminal connected to the RA header port; and
a second lead including a HIS electrode configured to be located proximate to the HIS bundle, the second lead including a proximal terminal configured to connect the HIS electrode to the LV header port;
sensing circuitry configured to sense cardiac activity (CA) signals over an LV sensing channel associated with the LV header port, wherein the CA signals are collected along a sensing vector defined at least in part by the HIS electrode;
memory configured to store program instructions;
one or more processors that, when configured to execute the program instructions:
measure an AV interval corresponding to an interval between i) an atrial paced (Ap) event or an atrial sensed (As) event, paced or sensed at the first electrode, and ii) a sensed ventricular (Vs) event sensed at the HIS electrode;
set a candidate AV delay based on the AV interval and based on a bundle branch adjustment (BBA) value;
measure a QRS characteristic of interest (COI) while utilizing the candidate AV delay in connection with delivering a pacing therapy by the IMD;
adjust the BBA value and reset the candidate AV delay based on the AV interval and the BBA value as adjusted;
repeat the adjust, reset and measure to obtain a collection of QRS COIs and corresponding candidate AV delays;
select one of the candidate AV delays, that corresponds to a select one of the QRS COIs, as a BBA AV delay; and
manage the pacing therapy, utilized by the IMD, based on the BBA AV delay, the candidate AV delays and BBA AV delays corresponding to candidate atrial-HIS (AH) delays and BBA AH delays, respectively, following a new As or Ap event before a pacing stimulus is delivered through the LV header port to the HIS bundle.

15. The system of claim 14, wherein the BBA value corresponds to a VV delay, the candidate AV delay based on a difference between the AV interval, and AV offset and the VV delay, the one or more processors further configured to adjust the BBA value based on multiple VV delays and resetting the candidate AV delay based on each of the corresponding multiple VV delays.

16. The system of claim 15, wherein the one or more processors are further configured to select the candidate AV delay having a corresponding VV delay that achieves the select one of the QRS COIs, the BBA AV delay corresponding to a BBA A-LV (HIS) delay representing a delay following a new As or Ap event before a pacing stimulus is delivered through the LV header port to the HIS bundle.

17. A method for managing atrial-ventricular (AV) delay adjustments, the method comprising:
providing a first lead having a first electrode configured to be located proximate to an atrial (A) site, the first lead having a proximal end with a first lead terminal connected to a right atrial (RA) header port of an implantable medical device (IMD); and
providing a second lead having a second electrode configured to be located proximate to at least one of a left bundle branch (LBB) site or a HIS bundle, the second lead having a proximal end with a second lead terminal connected to a right ventricular (RV) or left ventricular (LV) header port of the IMD;

utilizing one or more processors of the IMD for:
  measuring an AV interval corresponding to an interval between Ian atrial paced (Ap) event or an atrial sensed (As) event, paced or sensed at the first electrode, and ii a sensed ventricular (Vs) event sensed at the second electrode;
  setting a candidate AV delay based on the AV interval and based on a bundle branch adjustment (BBA) value, wherein the BBA value represents an adjustment to the AV interval to account for sensing the Vs event at the second electrode which is located proximate to at least one of a left bundle branch (LBB) site or a HIS bundle but connected to the RV or LV header port;
  measuring a QRS characteristic of interest (COI) while utilizing the candidate AV delay in connection with delivering a pacing therapy by the IMD;
  adjusting the BBA value and resetting the candidate AV delay based on the AV interval and the BBA value as adjusted;
  repeating the adjusting, resetting and measuring to obtain a collection of QRS COIs and corresponding candidate AV delays;
  selecting one of the candidate AV delays, that corresponds to a select one of the QRS COIs, as a BBA AV delay; and
  managing the pacing therapy, utilized by the IMD, based on the BBA AV delay.

18. The method of claim 17, wherein the pacing therapy corresponds to a DDD mode pacing therapy and the method further comprises providing the second electrode as an LBB electrode configured to be implanted into a septal wall to a depth sufficient to be located proximate to the LBB site, connecting the LBB electrode to the RV header port, sensing cardiac activity (CA) signals over an RV sensing channel where the CA signals are collected along a sensing vector defined at least in part by the LBB electrode.

19. The method of claim 17 wherein the selecting comprises selecting the one of the candidate AV delays that manages delivery of pacing pulses at the LBB site at a select point in time before an intrinsic wave front is expected to propagate to or beyond a corresponding point along a right bundle branch.

20. The method of claim 17, wherein the adjusting the candidate AV delay includes subtracting, from the AV interval, multiple candidate BBA values in order to time delivery of pacing pulses at the LBB site at a point in time fused with intrinsic waveform propagation to or beyond a corresponding point along a right bundle branch.

21. The method of claim 17, wherein the second electrode is an LBB electrode and wherein the pacing therapy corresponds to a cardiac resynchronization therapy (CRT) pacing therapy configured to deliver pacing pulses through the LV header port of the IMD to the LBB electrode at a depth within a septal wall sufficient to be located proximate to the LBB site.

22. The method of claim 17, further comprising providing, as the second electrode, a HIS electrode configured to be located at the HIS bundle, connecting the HIS electrode to the LV header port, sensing cardiac activity (CA) signals over an LV sensing channel where the CA signals are collected along a sensing vector defined at least in part by the HIS electrode, the candidate AV delays and BBA AV delays corresponding to candidate atrial-HIS (AH) delays and BBA AH delays, respectively, following a new As or Ap event before a pacing stimulus is delivered through the LV header port to the HIS bundle.

23. The method of claim 22, wherein the BBA value corresponds to a VV delay, the candidate AV delay based on a difference between the AV interval, and AV offset and the VV delay, the adjusting further comprising adjusting the BBA value based on multiple VV delays and resetting the candidate AV delay based on each of the corresponding multiple VV delays.

24. The method of claim 23, wherein the selecting further comprises selecting the candidate AV delay having a corresponding VV delay that achieves the select one of the QRS COIs, the BBA AV delay corresponding to a BBA A-LV (HIS) delay representing a delay following a new As or Ap event before a pacing stimulus is delivered through the LV header port to the HIS bundle.

25. The method of claim 17, further comprising providing, as the second electrode, a HIS electrode configured to be located at the HIS bundle, connecting the HIS electrode to a RV header port, sensing cardiac activity (CA) signals over an RV sensing channel where the CA signals are collected along a sensing vector defined at least in part by the HIS electrode, the candidate AV delays and BBA AV delays following a new As or Ap event before a pacing stimulus is delivered through the RV header port to the HIS bundle.

26. The method of claim 17, wherein the BBA value provides an adjustment to the AV interval to account for the Vs event being sensed at the second electrode when connected to the RV header port and located proximate to at least one of the LBB site or the HIS bundle.

27. The method of claim 17, wherein the BBA value provides an adjustment to the AV interval to account for the Vs event being sensed at the second electrode when located proximate to the LBB site and the second lead terminal is connected to the RV header port.

28. The method of claim 17, wherein the second electrode is configured to be located proximate to the HIS bundle and the second lead terminal is connected to the RV header port, the method further comprising providing a third lead having a third electrode configured to be located proximate to the LV and having a third lead terminal connected to the LV header port.

29. The method of claim 17, wherein the second electrode is configured to be located proximate to the HIS bundle and the second lead terminal is connected to the LV header port, the method further comprising providing a third lead having a third electrode configured to be located proximate to a right ventricular (RV) apex and having a third lead terminal connected to the RV header port.

30. A method for managing atrial-ventricular (AV) delay adjustments, the method comprising:
  providing electrodes configured to be located proximate to an atrial (A) site and at least one of a left bundle branch (LBB) site or a HIS bundle;
  utilizing one or more processors for:
    measuring an AV interval corresponding to an interval between an atrial paced (Ap) event or an atrial sensed (As) event and a sensed ventricular (Vs) event;
    setting a candidate AV delay based on the AV interval and a bundle branch adjustment (BBA) value;
    measuring a QRS characteristic of interest (COI) while utilizing the candidate AV delay in connection with delivering a pacing therapy by an implantable medical device (IMD);
    adjusting the BBA value and resetting the candidate AV delay based on the BBA value as adjusted;

repeating the adjusting, resetting and measuring to obtain a collection of QRS COIs and corresponding candidate AV delays;

selecting one of the candidate AV delays, that corresponds to a select one of the QRS COIs, as a BBA AV delay; and managing the pacing therapy, utilized by the IMD, based on the BBA AV delay, wherein the setting the candidate AV delay further comprises setting a candidate A-LV delay by adjusting the AV interval based on an AV offset and further subtracting a VV delay from the AV interval, the VV delay corresponding to the BBA value, the adjusting further comprising utilizing multiple candidate BBA values in order to time delivery of pacing pulses at the LBB site at a point in time fused with intrinsic waveform propagation to or beyond a corresponding point along a right bundle branch.

* * * * *